United States Patent
Quinn et al.

(10) Patent No.: US 9,913,858 B2
(45) Date of Patent: Mar. 13, 2018

(54) PREVENTION AND TREATMENT OF TOXICOSIS

(71) Applicants: Meat & Livestock Australia Limited, New South Wales (AU); Charles Sturt University, New South Wales (AU)

(72) Inventors: Jane Quinn, New South Wales (AU); Scott Edwards, New South Wales (AU); Martin Combs, New South Wales (AU)

(73) Assignees: MEAT & LIVESTOCK AUSTRALIA LIMITED, North Sydney, New South Wales (AU); CHARLES STURT UNIVERSITY, Wagga Wagga, New South Wales (AU)

( * ) Notice: Subject to any disclaimer, the term of this patent is extended or adjusted under 35 U.S.C. 154(b) by 0 days.

(21) Appl. No.: 15/038,312

(22) PCT Filed: Nov. 20, 2014

(86) PCT No.: PCT/AU2014/050363
§ 371 (c)(1),
(2) Date: May 20, 2016

(87) PCT Pub. No.: WO2015/074115
PCT Pub. Date: May 28, 2015

(65) Prior Publication Data
US 2016/0296554 A1 Oct. 13, 2016

(30) Foreign Application Priority Data
Nov. 20, 2013 (AU) .............................. 2013904517

(51) Int. Cl.
| | | |
|---|---|---|
| *A61K 33/00* | (2006.01) | |
| *A61K 33/06* | (2006.01) | |
| *A23K 20/20* | (2016.01) | |
| *A23K 20/22* | (2016.01) | |
| *A23K 50/10* | (2016.01) | |
| *A61K 9/00* | (2006.01) | |

(52) U.S. Cl.
CPC .............. *A61K 33/00* (2013.01); *A23K 20/20* (2016.05); *A23K 20/22* (2016.05); *A23K 50/10* (2016.05); *A61K 9/0019* (2013.01); *A61K 9/0053* (2013.01); *A61K 33/06* (2013.01)

(58) Field of Classification Search
CPC ........ A23K 50/10; A23K 20/20; A23K 20/22; A23K 20/24; A61K 33/00; A61K 9/0019; A61K 9/0053
See application file for complete search history.

(56) References Cited

U.S. PATENT DOCUMENTS

| | | | |
|---|---|---|---|
| 3,017,272 A * | 1/1962 | Van Dijck | .............. A23K 50/30 424/121 |
| 4,192,865 A | 3/1980 | Helbig | |
| 5,980,928 A | 11/1999 | Terry | |
| 2005/0277624 A1 | 12/2005 | Cook | |
| 2016/0296553 A1 | 10/2016 | Quinn et al. | |

FOREIGN PATENT DOCUMENTS

| | | |
|---|---|---|
| HU | 186119 B | 6/1985 |
| SU | 1246448 A1 | 2/1987 |
| UA | 22020 U | 4/2007 |
| WO | 2002085132 A1 | 10/2002 |
| WO | 2015/074114 A1 | 5/2015 |

OTHER PUBLICATIONS

Fielding et al., Pharmacokinetics and Clinical Utility of Sodium Bromide (NaBr) as an Estimator of Extracellular Fluid Volume in Horse, (2003), Journal of Veterinary Internal Medicine, 17:213-217.
Genicot et al., Wirksamkeit eines oralen Beruhigungsmittels auf das Verhalten and die zootechnischen Leistungen von Mastbullen der Weiβ-Blauen Belgischen Rasse, (1991), Journal of Veterinary Medicine A, 38:668-675.
Raidal et al., Pharmacokinetics of potassium bromide in adult horses, (2008), Australian Veterinary Journal, 86: 187-193.
Knight et al., Intoxication of Cattle with Sodium Bromide-Contaminated Feed, (1997), American Journal of Veterinary Research, 38:407-409.
Trepanier et al., Pharmacokinetic properties of bromide in dogs after the intravenous and oral administration of single doses., (1995), Research in Veterinary Science, 58:248-251.
U.S. Appl. No. 15/038,261.
USPTO; U.S. Appl. No. 15/038,261; Advisory Action dated Aug. 9, 2017.
USPTO; U.S. Appl. No. 15/038,261; Non-Final Office Action dated Nov. 29, 2016.
USPTO; U.S. Appl. No. 15/038,261; Final Office Action dated Apr. 14, 2017.
EPO; App. No. 14863191.4; European Extended Search Report for European Application dated Apr. 11, 2017.
Thodesen, Jorn et al.; "Feed intake, growth and feed utilization of offspring from wild and selected Atlantic salmon (Salmo salar)"; AKVAFORSK (Institute of Aquaculture Research); Aquaculture 180 (1999) 23 7-246; Apr. 26, 1999; pp. 237-246.
Monastyrev, A. M.; "Use of tranquilizers in transporting of cattle"; Donskoi S-kh. Inst.; Soversh. Tekhnol. Ved. Myasn. Skotovod. Prom. Osn. (1986), 101-4; published in 1986.
Genicot, B. et al.; "Efficiency of a sedative on the behaviour and the performances of Belgian white and blue double-muscled cattle during fattening"; Paul Parey Scientific Publishers, Berlin and Hamburg; J. Vet. Med. A 38, 668-675 (1991); Nov. 6, 1990 (includes English translation for German article).

(Continued)

*Primary Examiner* — Kyle Purdy
(74) *Attorney, Agent, or Firm* — Fitch, Even, Tabin & Flannery, LLP

(57) ABSTRACT

The invention described in this specification relates to the prevention and treatment of alkaloid-induced toxicosis in pasture grazing animals.

11 Claims, 13 Drawing Sheets

(56) References Cited

OTHER PUBLICATIONS

PCT; PCT App. No. PCT/AU2014/050363; Search report and opinion dated Dec. 17, 2014.
PCT; PCT App. No. PCT/AU2014/050362; Search report and opinion dated Dec. 16, 2014.
U.S. Appl. No. 15/038,261; Non-Final Office Action dated Jan. 19, 2018.

* cited by examiner

PREVENTION AND TREATMENT OF TOXICOSIS

CROSS-REFERENCE TO RELATED APPLICATION

This application is a U.S. national phase application of International Application No. PCT/AU2014/050363, filed Nov. 20, 2014, designating the United States, which claims priority to Australian Patent Application No. 2013904517, filed Nov. 20, 2013, which are incorporated by reference herein in their entirety.

FIELD OF THE INVENTION

This invention relates to the prevention and treatment of alkaloid-induced toxicosis (such as lolitrem B-induced toxicosis) in pasture grazing animals.

BACKGROUND OF THE INVENTION

Ryegrasses (genus *Lolium*) are commonly used to feed animals throughout the world. Such grasses can often be infected with endophyte fungi, such as those from the *Neotyphodium* genus. These fungi can live on these grasses and produce compounds (such as alkaloids) which can be useful to the plant. Some of these compounds can also be harmful to animals that consume the infected plant, and result in toxicosis.

One such example is the toxicosis resulting from the fungus *Neotyphodium lolii*, which produces the alkaloid lolitrem B in perennial ryegrass (*Lolium perenne*). This toxin forms a major component of the toxicosis called perennial ryegrass toxicosis (PRGT), or "Ryegrass Staggers", and can lead to neuromuscular dysfunction with symptoms such as tremors, staggers, ataxia, hyperaesthesia, tetany, gait abnormalities, increased severity of ill-coordination on movement and initial or continued sternal recumbency. These effects can be further exacerbated by external stimuli, and severe forms can lead to death of the animal, typically as a result of dehydration, starvation or attack by predators. Milder effects of lolitrem B-induced toxicosis can also have severe commercial outcomes, such as reduced live-weight gain, scouring and increased DAG formation, reduced fertility and low milk yields. The toxicoses that affect ruminants grazing *Phalaris* also cause tremors and other neurological and systemic clinical signs to those observed in respect of PRGT.

There is currently no known cure for treating animals with lolitrem B intoxication, PRGT or *Phalaris* toxicosis and the subsequent animal morbidity and mortality impacts adversely on animal welfare and results in enormous losses in animal production revenue. Animals may recover from such conditions if they can be moved away from the infected pastures. However, this is not always possible, especially where large pasture areas are infected and many animals are grazing on that pasture.

Whilst endophyte-infected pastures can be removed and replaced with grass that is not infected, this is of great effort and cost to achieve and is not always successful. The replacement grass may also not be as viable as the endophyte-infected pasture because it may be more prone, for example, to drought, due to the loss of the protective effects that the endophytes provide to the plants. Similarly, it is difficult to ensure that the endophyte infected seed is completely removed from the pasture, which may result in re-infection. Removal and replacement of endophyte-infected pastures is therefore not always performed.

It is also difficult and time-consuming to test for the endophytes. Testing can only be performed by laboratory analysis, and representative samples taken from a large spread of the pasture need to be carefully collected and tested within a short time frame. Testing is therefore not always practical and may not be accurate depending on factors such as the samples selected and submitted, and the transportation conditions of the samples to the laboratory.

There have been several other approaches investigated to overcome the problems of endophyte-induced toxicosis. A grass modified to be unfavourable to endophyte infection may overcome the problem of pasture re-infection. However, similarly to the replacement pastures, as the endophytes also provide the plant with benefits such as resistance to drought and protection from insects, this approach can still greatly disadvantage the plant and viability of the pastures.

Another approach has been to investigate the selective breeding or genetic modification of the endophyte to maximise its positive effects on the plant (e g insecticide properties) whilst minimising the expression of the toxicosis-causing alkaloids. These approaches, however, are expensive and have been shown to be not completely effective and/or commercially practical across all levels of farming.

Another approach includes feeding animals additives to overcome the toxicity of the alkaloids. An example of this is outlined in patent application WO 00/65928, whereby a modified yeast cell wall and a mineral clay is fed to animals to inactivate the ergot alkaloids causing fescue toxicosis, by binding the alkaloids within the gastrointestinal tract (before their systemic absorption). This treatment does not interfere with the pharmacodynamics of the endophytic alkaloid, but prevents its absorption. As such, this approach does not treat the symptoms of fescue toxicosis, but can minimise the effect of the alkaloids on the animal.

Whilst these approaches have each displayed some success, none have been able to significantly reduce the impact of alkaloid-induced toxicosis using a practical, commercially viable technique.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

This invention relates to the prevention and/or treatment of alkaloid-induced toxicosis in animals. In particular, it relates to the prevention and/or treatment of perennial ryegrass toxicosis, *phalaris* toxicosis and fescue grass toxicosis in animals that graze on these grasses.

In one embodiment the invention provides a method of preparing an animal for grazing in a selected pasture. The method seeks to prevent symptoms of lolitrem B toxicity from developing in the animal during or at completion of grazing in the pasture. The method includes the step of administering a formulation including bromide to an animal selected for grazing in a selected pasture in an amount effective for preventing the animal from developing symptoms of lolitrem B toxicity. The formulation is to be administered to the animal before release of the animal to the pasture for grazing.

The present invention also provides a method of treating symptoms of lolitrem B toxicity in an animal, the method including administering bromide to an animal having symptoms of lolitrem B toxicity. In one embodiment, the symptoms have been acquired through pasture grazing.

The present invention also provides use of bromide in the manufacture of a formulation for preventing symptoms of lolitrem B toxicity from developing in an animal during, or at the completion of, pasture grazing, the formulation for administration to the animal prior to release of the animal for pasture grazing.

The method also seeks to prevent symptoms of *Phalaris* toxicity from developing in the animal during, or at completion of, grazing in the pasture. The method includes the step of administering a formulation including bromide to an animal selected for grazing in a selected pasture in an amount effective for preventing the animal from developing symptoms of *Phalaris* toxicity. The formulation is to be administered to the animal before release of the animal to the pasture for grazing.

The present invention also provides a method of treating symptoms of *Phalaris* toxicity in an animal, the method including administering bromide to an animal having symptoms of *Phalaris* toxicity. In one embodiment, the symptoms have been acquired through pasture grazing.

The present invention also provides use of bromide in the manufacture of a formulation for preventing symptoms of *Phalaris* toxicity from developing in an animal during, or at the completion of, pasture grazing, the formulation for administration to the animal prior to release of the animal for pasture grazing.

In one embodiment, the bromide may be administered orally, intravenously or intra-peritoneally. In another embodiment, the bromide is in the form of a salt such as potassium bromide, sodium bromide or magnesium bromide. Most preferably, the bromide salt is in the form of potassium or magnesium bromide, which are useful for oral administration. Sodium bromide is useful for intravenous administration.

The present invention also relates to a formulation for use in preparing an animal for pasture grazing to prevent symptoms of lolitrem B toxicity from developing in the animal during or at completion of grazing, the formulation including bromide in an amount for preventing symptoms of lolitrem B toxicity developing in the animal, the formulation for administration prior to release of the animal for pasture grazing.

The present invention also relates to a formulation for use in preparing an animal for pasture grazing to prevent symptoms of *Phalaris* toxicity from developing in the animal during, or at completion of, grazing, the formulation including bromide in an amount for preventing symptoms of *Phalaris* toxicity developing in the animal, the formulation for administration prior to release of the animal for pasture grazing.

In one embodiment, the animal is a ruminant (e.g. ovine, bovine or caprine).

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
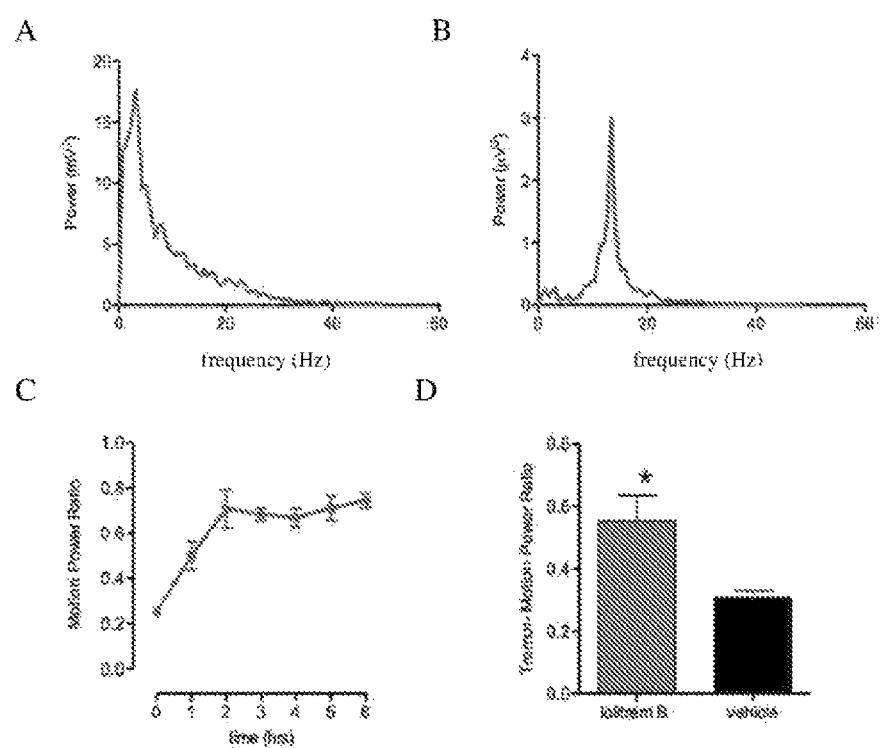
FIG. 1. Tremor analysis of animals treated with a single dose of lolitrem B toxin. Tremor analysis: FFT frequency analysis from a mouse prior to (A) and 6 hours post lolitrem B injection 2 mg/kg i.p. (B). Low frequency (0-7 Hz) power output represents primarily movement. (C) Tremor-Motion power ratio reveals tremor accounting for an increasing proportion of movement even at 6 hours. (D) Tremor-Motion power ratio at one hour post lolitrem B injection (n=4) and vehicle only control (n=4) (*p<0.05, lolitrem B (2 mg/kg i.p.) vs vehicle).

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many uses and methods of treatment similar or equivalent to those described herein, which could be used in the practice of the present invention. The present invention is in no way limited to the specific methods and materials described.

It will be appreciated that the invention has two major applications. In one aspect, the invention will be used in the treatment of animals suffering from lolitrem B toxicity. In another aspect, the invention will be used in a prophylactic manner to prevent the development of the toxicosis symptoms in the animal. Prevention of such disorders may be particularly useful during peak seasons of endophyte growth, which can be predictable in some regions.

The invention is well-suited to preventing and treating toxicosis resulting from endophyte-infected or endophyte-prone grasses, such as perennial ryegrasses, *Phalaris* or fescue grasses. This includes toxicosis induced by compounds produced by endophytes (such as those from the *Neotyphodium* genus), which can form a symbiotic relationship with such grasses. For example, the toxicosis may be due to *Neotyphodium lolii* infection of the grass.

The compounds inducing the toxicosis may be alkaloids. An example is an indole-diterpenoid, such as lolitrem B. Another example is an ergot alkaloid, such as ergovaline. In particular, the invention relates to the treatment and prevention of symptoms caused by lolitrem B toxicity.

The invention can be used on any pasture-grazing animal that has developed, or is at risk of developing, symptoms of lolitrem B toxicity. In particular, the invention relates to the prevention and treatment of symptoms of lolitrem B toxicity in animals feeding on grass, and more particularly, perennial ryegrass, *Phalaris* or fescue grass. Whilst this invention relates to any pasture-grazing animal, the invention is preferably directed towards ruminants including cattle, sheep, goats, camels, llamas, alpacas and deer. In a certain embodiment, the animal may be a hindgut fermenter such as a horse or a rabbit. The invention is also not intended to cover humans. Therefore, in one embodiment, the animal is not a human.

As mentioned above, symptoms of lolitrem B toxicity include tremors, staggers, ataxia, hyperaesthesia, tetany, and gait abnormalities resulting in increased severity of ill-coordination of movement and initial or continued sternal or lateral recumbency. An animal having these symptoms, as well as others that are recognised as being indicative of PRGT, can be treated according to the present invention. Therefore, in one embodiment, the animal is first assessed as having developed, or being likely to develop, symptoms of lolitrem B toxicity. Diagnosis or likely development of PRGT and fescue toxicosis may be determined by any one of the following: specific toxicological testing of pasture samples, by the Keogh tremor scale, by the presence of severe neurological signs consistent with PRGT (as listed above), by a previous history of PRGT on the property, by prolonged exposure to pastures containing perennial ryegrass, by the presence of other animals within the pasture showing severe neurological signs consistent with PRGT, and by histopathology findings consistent with a diagnosis of PRGT. This may be further indicated by the absence of clinical or neurological signs indicating any other disease aetiology. A person skilled in the art will understand that "symptoms", as used herein, is the equivalent of "clinical signs".

Successful treatment of the animal will be achieved when one or more of the symptoms mentioned above are completely or partially resolved. For example, the animal's tremors may cease completely, while any staggers exhibited by the animal may decrease to the point where they no longer pose a concern for the animal's ability to function normally (e.g. the animal is able to access drinking water and feed itself). In addition, the growth performance of the animal will improve (e.g. the animal's weight, reproductive performance and milk production will return to normal levels, and tremor and movement abnormalities will resolve).

In the context of prevention, the animal to be administered bromide will be any pasture grazing animal that is at risk of developing symptoms of lolitrem B toxicity. That is, the animal is one that may, through grazing on grass infected with endophyte fungus, develop symptoms of toxicosis. Therefore, in one embodiment, the animal is first assessed as being at risk of developing symptoms of lolitrem B toxicity. To prevent toxicosis, a pasture-grazing animal will therefore generally be given bromide before it is released into a pasture for grazing.

In one embodiment, the animal does not have stress-related or stress-induced inappetance at the time of administration of bromide. In one embodiment, the feed intake of the animal up to the time of administration of bromide has been normal. In one embodiment, the animal is not suffering from grass toxicosis at the time of administration of bromide. In one embodiment, the animal does not have a movement disorder at the time of administration of bromide.

As mentioned above, peak seasons of endophyte growth are predictable in some regions, and therefore bromide may only be administered to an animal during particular times of the year. In one embodiment, bromide (e.g. a formulation containing bromide) is administered for a period of one day to no more than two weeks from release of the animal to the selected pasture for grazing. Bromide may also be administered on a daily basis, for example, for seven to 10 days before the animal is released into a pasture (i.e. before grazing). It may also be administered after release (for example, for several months) of the animal into the pasture (i.e. during grazing). For example, the bromide may be administered to the animal for one month, two months, three months, four months, five months, or more, after release of the animal into the selected pasture. Further, bromide may be administered for up to 14 days after the animal has been removed from the pasture (i.e. after grazing).

Bromide may also be administered via a slow release intra-ruminal capsule. Successful prevention of toxicosis will be achieved when the animal does not develop any, or only develops to an insignificant extent, symptoms of toxicosis. In addition, the growth performance of the animal will not be adversely affected (e.g. the animal's weight and milk production will remain at normal levels, the reproductive performance will not be impeded, and conditions such as fescue foot will not develop).

A dose of a bromide-containing formulation of the invention may be delivered at once, for example, as a bolus, or over the course of several hours.

Theoretically there is no maximum limit for the dosage provided that the bromide does not accrue in the animal to a point whereby it diminishes the quality of the animal or products therefrom.

The bromide may be provided in the form of a formulation adapted for delivery by an animal handler, or for consumption by the animal. Examples are described herein.

It will be understood that the specific dose level of bromide for any particular animal may depend upon a variety of factors including the activity of the specific bromide employed, the age, body weight, general health, sex and/or diet of the animal, time of administration, route of administration, and rate of excretion, drug or supplement combination (i.e. other drugs or supplements being used concomitantly with the bromide), and the severity of the toxicosis being exhibited, if being used as a treatment.

To prevent or treat symptoms of lolitrem B toxicity, bromide (e.g. in a formulation including bromide) may be administered to the animal in an amount of about 10 to about 750 mg/kg per dose. For example, the bromide may be administered to the animal in an amount of about 10 to about 650 mg/kg, or about 10 to about 500 mg/kg. A dose of about 10 to about 500 mg/kg is preferred for intravenous administration. A dose of about 10 to about 750 mg/kg is preferred for oral administration. Bromide (e.g. in a formulation including bromide) may be administered to the animal in an amount of about 10 mg/kg, about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg or about 750 mg/kg per dose.

In one embodiment, to prevent or treat symptoms of lolitrem B toxicity, the bromide (e.g. in a formulation including bromide) is administered in an amount to provide an animal with about 10 to about 750 mg/kg animal weight of bromide. For example, the bromide may be administered or provided in an amount to provide the animal with from about 20 to about 600 mg/kg animal weight (e.g. from about 40 to about 500 mg/kg animal weight, from about 60 to about 400 mg/kg animal weight, or from about 100 to about 300 mg/kg) of bromide. In one embodiment, the bromide is in an amount to provide an animal with about 300 mg/kg animal weight of bromide.

Bromide (e.g. in a formulation including bromide) may be administered to provide an animal with about 10 mg/kg, about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg, about 500 mg/kg, about 550 mg/kg, about 600 mg/kg, about 650 mg/kg, about 700 mg/kg or about 750 mg/kg animal weight of bromide.

For repeated daily administration (e.g. for prophylactic purposes or after an initial loading dose, where it is desired to maintain serum levels of bromide for prolonged periods), a suitable dose of bromide is about 0.5 to about 30 mg/kg (for oral administration) and about 0.4 to about 25 mg/kg (for intravenous administration).

In one embodiment, bromide is the only active in the formulation. In one embodiment, bromide is the only active provided to the animal. Therefore, in one embodiment, the invention does not include providing therapeutic or nutritive agents, other than bromide, to the animal. Examples of such agents include electrolytes (e.g. sodium, potassium, magnesium, manganese, chromium, and calcium, and chloride, oxide, carbonate and aspartate salts thereof), amino acids (or salts thereof), and sources of energy (e.g. sugar). In one embodiment, the invention does not include providing a modified yeast cell wall and a mineral day to the animal.

Suitable formulations for use in the present invention include drenches, gels, pastes, tablet/bolus formulations, gelatin capsules, injectable formulations, or intra ruminal devices for slow release of the active.

In one embodiment the invention provides a drench including bromide, wherein the drench comprises bromide in an amount to provide an animal with about 20 to about 500 mg bromide/kg animal weight. In one embodiment, the drench includes bromide in an amount to provide an animal with about 20 to about 400 mg/kg animal weight (e.g. from about 30 to about 300 mg/kg, from about 50 to about 400 mg/kg, or from about 100 to about 300 mg/kg animal weight) of bromide. In one embodiment, the drench includes bromide in an amount to provide an animal with about 300 mg/kg animal weight of bromide.

In one embodiment, the drench includes bromide in an amount to provide an animal with about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg or about 500 mg/kg animal weight of bromide.

Preferred drenches are those adapted for use in a ruminant animal, particularly sheep (i.e. ovine) or cattle (i.e. bovine). Preferably the concentration of bromide in the drench is from about 5 to about 70% w/v (liquid or paste formulation) and about 5 to about 70% w/w (powder or solid formulation). In one embodiment, the concentration of bromide in the drench is from about 10 to about 60%, from about 20 to about 50%, or from about 30 to about 40% w/v or w/w. In one embodiment, the concentration of bromide in the drench is about 5, about 10, about 20, about 30, about 40, about 50, about 60 or about 70% w/v or w/w.

In one embodiment, the only active in the drench is bromide.

In another embodiment the invention provides an injectable formulation including bromide, wherein the formulation comprises bromide in an amount to provide an animal with about 10 to about 500 mg bromide/kg animal weight of bromide. In one embodiment, the injectable formulation includes bromide in an amount to provide an animal with about 20 to about 400 mg/kg animal weight (e.g. from about 30 to about 300 mg/kg animal weight, from about 50 to about 400 mg/kg animal weight or from about 100 to about 300 mg/kg animal weight) of bromide. In one embodiment, the injectable formulation includes bromide in an amount to provide an animal with about 300 mg/kg animal weight of bromide.

In one embodiment, the injectable formulation includes bromide in an amount to provide an animal with about 10 mg/kg, about 20 mg/kg, about 50 mg/kg, about 75 mg/kg, about 100 mg/kg, about 120 mg/kg, about 150 mg/kg, about 200 mg/kg, about 250 mg/kg, about 300 mg/kg, about 350 mg/kg, about 400 mg/kg, about 450 mg/kg or about 500 mg/kg animal weight of bromide.

In one embodiment, the only active in the injectable formulation is bromide.

Preferably the formulation is adapted for application to sheep or cattle. Preferably the concentration of bromide is from about 5 to about 70% (w/v). In one embodiment, the concentration of bromide in the formulation is from about 10 to about 60%, from about 20 to about 50%, or from about 30 to about 40% (w/v). In one embodiment, the concentration of bromide in the formulation is about 5, about 10, about 20, about 30, about 40, about 50, about 60 or about 70% (w/v).

The drench or injectable formulation may be provided in the form of a kit including written instructions enabling use of the kit in a method described above. In one embodiment, the invention provides a kit including a drench, as described herein, and written instructions enabling use of the kit in a method described herein. In one embodiment, the invention provides a kit including an injectable formulation, as described herein, and written instructions enabling use of the kit in a method described herein.

The bromide may be provided in the form of a supplement in liquid (e.g. an aqueous solution) or solid form that is to be consumed by the animal. It will be evident that, given the variable consumption of solids and liquids by animals, the amount of bromide in a consumable composition as stated above is approximate and may be varied depending on the type of formulation (solid v. liquid), the solubility of the bromide, the body weight of the animal and the average solid and liquid intake of the animal. Supplements may be provided with carriers, or may be formulated into feed with binders. Exemplary carriers include grain or grass by-products, such as oats, barley, wheat, canals, rye, sorghum, millet, corn, legumes and grasses.

In one embodiment, bromide is provided with a feed in an amount of between about 0.01 to 5% w/w dry matter. For example, bromide may be provided in an amount of between about 0.5 and 4% or 1 and 3% why dry matter. In one embodiment, the concentration of bromide in feed is about 0.01, about 0.1, about 0.2, about 0.5, about 1, about 2, about 3, about 4 or about 5% w/w dry matter.

The bromide may be administered with another medication (e.g. an antibiotic), a growth promotant or incorporated into a mineral pre-mix. Suitable amounts of bromide in this regard include between about 0.1 and about 60% w/w dry weight. For example, bromide may be provided in an amount of between about 0.5 and about 50%, about 1 and about 40%, about 5 and about 30% or about 10 and about 20% w/w dry weight. In one embodiment, the concentration of bromide is about 0.1, about 0.2, about 0.5, about 1, about 2, about 5, about 10, about 15, about 20, about 25, about 30, about 35, about 45, about 50, about 55 or about 60% w/w dry matter.

Specific examples include:
1. IV injection—single bolus high dose of NaBr for acute cases. Solution to be used to have a bromide concentration of 10 to 70% w/v. Bromide dose: 10 to 500 mg/kg.
2. Oral—for a rumen drench (single phase release liquid, paste or solid formulation): fast release complete within 6 to 24 hours. For prophylaxis or treatment, dose lasting up to 3 weeks. This can be given at the observation of mild clinical signs or as a prophylactic dose prior to PRGT critical periods. Drench to contain bromide 10-70% w/v or w/w. Bromide dose: 10 to 500 mg/kg.
3. Oral—intra-ruminal device—slow or dual release formulation: fast release for priming dose and slow release for maintenance dose lasting up to 6 weeks. This can be given at the observation of mild clinical signs or as a prophylactic dose prior to PRGT critical periods. Formulation to contain bromide 10 to 70% w/v or w/w. Bromide dose: 600 mg/kg.
4. Oral—as a feed additive—the bromide may be provided in the form of a supplement in liquid or solid form that is to be consumed by the animal. It will be evident that, given the variable consumption of solids and liquids by animals, the amount of bromide in a consumable composition is approximate and may be varied depending on the type of formulation (solid versus liquid), the solubility of the bromide, the body weight of the animal and the average solid and liquid intake of the animal. Supplements may be provided with carriers, or may be formulated into feed with binders. Exemplary carriers include grain or grass by products, such as oats, barley, wheat, canola, rye, sorghum, millet, corn, legumes and grasses. Inclusion of bromide in an antibiotic or mineral pre-mix at 0.1 to 60% w/w is a practical method of administering bromide to achieve a dose of 10 to 750 mg/kg. Overall, bromide is incorporated into the ration at a rate of 0.01 to 5% w/w dry matter. This delivery can be used after, or in addition to, deliveries 1 & 2.
5. In an on-farm outbreak of PRGT, animals might receive on a basis of individual need a combination of more than one administration form and/or dose depending on progression of their disorder and/or amelioration of their clinical signs on return to pastures.

As used herein, "bromide" refers to the bromine ion ($Br^-$). It will be understood by a person skilled in the art that bromide will generally be administered to the animal in the form of a salt and/or other compound with a bromine group that readily dissociates in situ and/or in vivo to give bromide. Preferably, the bromide is in the form of a salt, which may contain an alkali metal or alkaline earth metal. For example, the bromide may be in the form of potassium bromide, sodium bromide or magnesium bromide. Potassium bromide and magnesium bromide are particularly useful for oral administration and sodium bromide is useful for intravenous administration. Magnesium bromide has a higher percentage of bromide than both the potassium and sodium salts, and possesses much greater water solubility than both the potassium and sodium salts. Consequently, magnesium bromide solutions can be made at much higher bromide concentrations than other salts, before saturation is reached. This property of the magnesium salt of bromide impacts on formulation; low volume delivery is practically and economically advantageous.

Bromide may be administered to an animal by several different routes, including those selected from orally, buccally, nasally, vaginally, rectally, topically, subcutaneously, intramuscularly, intraruminally, intravenously, intraperitoneally and transdermally. Preferably, the bromide is administered to the animal orally, intraveneously or intraperitoneally. Most preferably, the bromide is administered to the animal orally.

In one embodiment, the formulation includes, in addition to the bromide, one or more pharmaceutically-acceptable excipients, such as binders, disintegrants, dispersants, lubricants, colours, flavours, coatings, glidants, sorbents, absorption-enhancing agents, emulsifiers, surfactants, buffers, bulking agents, tonicity-adjusting agents, preservatives, wetting agents, solvents, and sweeteners. Suitable examples of excipients to include in formulations for use in the invention are well-known to a person skilled in the art.

In one embodiment, the bromide is administered or given to the animal in an aqueous solution. For example, the bromide can be dissolved in the animal's drinking water for the animal to consume. The bromide may be incorporated into animal feed as a means to administer the bromide to the animal and/or encourage the animal to consume the bromide (as discussed above). Animal feed includes any food that the animal is capable of ingesting and if desired, any additional ingestable materials. For example, it could include grass, plant extracts, vitamins, minerals, feed supplements and other such materials.

In one aspect, the invention provides a pharmaceutical composition including an effective amount of a bromide and one or more pharmaceutically acceptable excipients for use in preventing symptoms of lolitrem B toxicity from arising in an animal selected for pasture grazing.

The present invention also provides a pharmaceutical composition including an effective amount of bromide and one or more pharmaceutically acceptable excipients for use in preparing an animal for pasture grazing to prevent symptoms of lolitrem B toxicity from arising in the animal during, or at completion of, grazing.

The invention also relates to the use of a therapeutically effective amount of bromide for preparing an animal for grazing in a selected pasture to prevent symptoms of lolitrem B toxicity from developing in the animal during or at completion of grazing in the pasture, including administering a formulation including bromide to the animal selected for grazing in a selected pasture in an amount effective for preventing the animal from developing symptoms of lolitrem B toxicity before release of the animal to the pasture for grazing.

The present invention also provides a pharmaceutical composition for use in preparing an animal for grazing in a selected pasture to prevent symptoms of lolitrem B toxicity from developing in the animal during, or at completion of, grazing in the pasture, in any of the embodiments described in the specification.

The present invention also relates to the use of a therapeutically effective amount of bromide for the manufacture of a medicament for preparing an animal for grazing in a selected pasture to prevent symptoms of lolitrem B toxicity from developing in the animal during, or at completion of, grazing in the pasture.

The present invention also relates to bromide when used in a method of preparing an animal for grazing in a selected pasture to prevent symptoms of lolitrem B toxicity from developing in the animal during, or at completion of, grazing in the pasture.

The present invention also relates to a composition having an active ingredient for use in preparing an animal for grazing in a selected pasture to prevent symptoms of lolitrem B toxicity from developing in the animal during, or at completion of, grazing in the pasture, wherein the active ingredient is bromide.

The present invention also relates to the use a formulation containing bromide in preparing an animal for grazing in a selected pasture to prevent symptoms of lolitrem B toxicity from developing in the animal during, or at completion of, grazing in the pasture, such as described above.

In one embodiment, bromide is the only active in the formulation or composition.

The present invention also provides a pharmaceutical composition including an effective amount of bromide and one or more pharmaceutically acceptable excipients for use in treating symptoms of lolitrem B toxicity in an animal having the symptoms acquired through pasture grazing.

The invention also provides use of a therapeutically effective amount of bromide for treating symptoms of lolitrem B toxicity in an animal having the symptoms acquired through pasture grazing, including administering a formulation including bromide to the animal.

The present invention also provides a pharmaceutical composition for use in treating symptoms of lolitrem B toxicity in an animal having the symptoms acquired through pasture grazing, in any of the embodiments described in the specification.

The present invention also relates to the use of a therapeutically effective amount of bromide for the manufacture of a medicament for treating symptoms of lolitrem B toxicity in an animal having the symptoms acquired through pasture grazing.

The present invention also relates to bromide when used in a method of treating symptoms of lolitrem B toxicity in an animal having the symptoms acquired through pasture grazing.

The present invention also relates to a composition having an active ingredient for use in treating symptoms of lolitrem B toxicity in an animal having the symptoms acquired through pasture grazing, wherein the active ingredient is bromide.

The present invention also relates to the use a formulation containing bromide in treating symptoms of lolitrem B toxicity in an animal having the symptoms acquired through pasture grazing, such as described above.

In one embodiment, bromide is the only active in the formulation or composition.

The clinical signs or symptoms of lolitrem B-induced toxicosis overlap, to a significant extent, with the symptoms of *Phalaris* toxicosis. For example, *Phalaris* toxicosis includes symptoms such as partial paralysis, ataxia, generalised muscle tremor, incoordination and proprioceptive deficits with frequent falling over, and the inability to rise after falling. Animals may also appear hyperaesthetic and struggle when approached. While the identity of the toxins responsible for *Phalaris* toxicosis is not known, the neurotoxicological pathways through which lolitrem B and the toxins responsible for *Phalaris* toxicosis act are very similar. Therefore, it would be clear to a person skilled in the art that the methods and formulations of the present invention, as described above, can also be used in the prevention and treatment of *Phalaris* toxicosis.

Accordingly, the present invention also relates to a method of preparing an animal for grazing in a selected pasture to prevent symptoms of *Phalaris* toxicity from developing in the animal during, or at completion of, grazing in the pasture, including administering a formulation including bromide to the animal selected for grazing in a selected pasture in an amount effective for preventing the animal from developing symptoms of *Phalaris* toxicity before release of the animal to the pasture for grazing.

The present invention also relates to a formulation for use in preparing an animal for pasture grazing to prevent symptoms of *Phalaris* toxicity from developing in the animal during, or at completion of, grazing, the formulation including bromide in an amount for preventing symptoms of *Phalaris* toxicity developing in the animal, the formulation for administration prior to release of the animal for pasture grazing.

The present invention also relates to a method of treating symptoms of *Phalaris* toxicity in an animal including administering bromide to an animal having symptoms of *Phalaris* toxicity.

EXAMPLES

Example 1

Lolitrem B was tested in mice to establish this as a suitable model for perennial ryegrass toxicosis and lolitrem B intoxication in grazing animals. Lolitrem B (in a dose of 2 mg/kg) administered intraperitoneally (IP) produced a decrease in movement and a distinctive tremor spike in the range of 10-19 Hz. These signs are consistent with clinical signs seen in grazing animals (See FIG. 1).

Example 2

Bromide Alleviates/Prevents Clinical Signs of Lolitrem B Intoxication in a Rodent Model of PRGT.

To investigate the potential of bromide as a therapeutic agent for perennial ryegrass toxicosis and lolitrem B intoxication in grazing animals. Mice were administered 2500 ppm KBr in their drinking water for 7 days prior to injection with lolitrem B (2 mg/kg IP). Mice demonstrated reduced tremor to movement ratio and reduced peak tremor frequency at one hour post injection. Animals tested in a novel arena test at 3.5 hours post lolitrem B injection (2 mg/kg IP) demonstrated increased movement and reduce time freezing. This provides strong evidence that bromide can alleviate or prevent clinical signs of perennial ryegrass toxicosis and lolitrem B intoxication (See FIGS. 2 to 5).

Example 3

Determination of Pharmacokinetics of Bromide in Sheep after Single Intravenous (IV) and Oral (PO) Doses Sixteen Merino sheep were randomly assigned to two treatment groups. The intravenous (IV) group were given 120 mg/kg bromide, as sodium bromide. The per os (PO-oral) group were given 120 mg/kg bromide, as potassium bromide. Serum bromide concentrations were determined by colorimetric spectrophotometry.

Animals:

Sixteen sheep, weighing between 49.5 kg and 67 kg and with an average body condition score of >2 were randomly divided into equal number (IV and PO treatment groups). Animals were placed in individual feeding pens and were fed twice daily on a ration of oats and lupins as well as ad libitum hay and water. Estimated chloride content for oats and lupins was 0.11% and 0.4% respectively.

Indwelling intravenous cannulas (Braun, Certo Splittocan 335, 16 gauge, 32 cm) were placed into the left jugular vein and secured with 2/0 polypropylene suture. A 25 cm low volume IV extension set (BMDi TUTA, 25×m minimal volume IV extension set) was connected to the catheter hub and the area was then bandaged.

Sodium bromide (NaBr) (Sigma-Aldrich) and potassium bromide (KBr) (Sigma-Aldrich) solutions were prepared using sterile water. The prepared NaBr solution was then filtered through a microfilter (0.22μ MILLEX GP, Cork, Ireland). Sodium and potassium salts were administered to dose sheep with 120 mg/kg of Br (154.6 mg/kg NaBr or 178.8 mg/kg KBr). All serum concentrations are for Br. Potassium bromide is the most readily available form of Br for oral therapy. Sodium bromide was used for the IV study because of cardiotoxicity associated with potassium. Both salts are fully disassociated in solution therefore no PK differences were expected.

IV Bromide:

NaBr solution was administered through the cephalic vein using a 21 gauge needle over a period of 1 minute. Sheep were restrained in a seated position. Blood samples were collected at 0, 1, 5, 10, 15, 20 and 30 min and then at 1, 2, 3, 4, 6, 8, 10, 12, 24 h. Samples thereafter were collected at 12 h intervals to 240 h then at 24 h intervals to 336 h. A final sample was taken at 528 h. For each sample, the initial 2 mL of blood collected was discarded and a sterile syringe used to withdraw 5 mL of blood which was then placed into a plain separator blood tube (Vacuette: Greiner Bio-one). The cannulas were flushed with 3 mL of 5% heparinised saline after each collection. Each blood sample was left to stand for 30 min before centrifugation at 2000 g for 5 min. Serum was harvested and stored at −20° C. until analysis.

PO Bromide:

KBr solution was administered via an orogastric tube, then flushed with 500 mL water. Blood samples were collected at 0, 1, 2, 3, 4, 6, 8, 10, 12, 24 h, then at 12 h intervals to 240 h, then at 24 h intervals to 336 h. A final sample was taken at 504 h. When collecting blood samples at 1 h through to 10 h the rumen was auscultated, over the caudo-dorsal blind sack, to determine if the high salt load affected rumen motility.

Determination of Serum Bromide Concentrations:

Serum Br concentrations were determined by calorimetric spectrophotometry as previously described (Tietz, 1976), with some modification. Briefly, 0.35 mL of serum was added to 3.15 mL of 10% trichloroacetic acid (Sigma-Aldrich) in a 10 mL centrifuge tube, vortexed, then centrifuged for 15 min at 2000 g. 2.5 mL of supernatant was then mixed with 0.25 mL of 0.5% $Au_2Cl_6$ (Sigma-Aldrich) and left to stand for 30 min. Absorbance was measured with a spectrophotometer at 440 nm. The standard curve was linear in the range of 25 μg/mL to 5000 μg/mL, $R^2$=0.9992. The lower limit of quantification was 25 μg/mL.

Pharmacokinetics:

Maximum concentration ($C_{max}$) of Br and time to $C_{max}$ ($T_{max}$) were determined directly from the data. Other PK parameters were determined for each sheep by use of non-compartmental analysis with a commercial software program (Topfit 2.0, Gustav Fischer Verlag). Area under the curve ($AUC_{0-\infty}$) and area under the first moment curve ($AUMC_{0-\infty}$) were calculated by the linear trapezoidal rule (Gibaldi, 1982) the terminal elimination rate constant ($\Delta_z$) was calculated by means of log-linear regression. Whereas parameters $C_{max}$, $T_{max}$, and AUC (where bioavailability is not absolute) are expected to differ when given IV or PO, $t_{1/2}$ should be the same, irregardless of route of administration. A t-test of the hypothesis of no difference between the $t_{1/2}$ population means was performed. All results are expressed as mean±standard deviation (SD).

After IV administration the maximum concentration ($C_{max}$) was 822.11±93.61 mg/L, volume of distribution ($V_d$) was 0.286±0.031 L/kg and the clearance (Cl) was 0.836±0.255 mL/h/kg. After PO administration the $C_{max}$ was 453.86±43.37 mg/L and the time of maximum concentration ($T_{max}$) was 108±125 h. The terminal half-life ($t_{1/2}$) of bromide after IV and PO administration was 387.93±115.35 h and 346.72±94.05 h, respectively. The oral bioavailability (F) of bromide was 92%. No adverse reactions were noted during this study in either treatment group. The concentration versus time profiles exhibited secondary peaks, suggestive of gastrointestinal cyclic redistribution of the drug.

All sheep in the PO group exhibited no discernable neurological effects. There was no observed alteration in rumen motility and animals continued to eat and drink. Assessment of any acute neurological effects correlating with peak Br concentration following IV administration was difficult as the sheep were held in the seated position throughout the initial 20 min, for ease of sampling. All IV sheep walked back to their individual pens and subjectively observers reported a mild tranquilising effect for approximately 1 to 2 h post-injection.

The relevant non-compartmental pharmacokinetic parameters derived from this study are summarised in Table 1.

TABLE 1

Pharmacokinetic parameters (mean ± SD) of bromide after intravenous and per oral administration to eight sheep at a dose of 120 mg/kg.

| Pharmacokinetic variable | Intravenous administration (mean ± SD) | Oral administration (mean ± SD) |
|---|---|---|
| $C_{max}$ (mg/L) | 822.11 ± 93.61 | 453.86 ± 43.37 |
| $T_{max}$ (h) | — | 108 ± 124.86 |
| $AUC_{0-\infty}$ (mg*h/L) | 157221.8 ± 52681.53 | 143948.9 ± 26156.16 |
| $MRT_{0-\infty}$ (h) | 545.5 ± 226.1 | 413.4 ± 150 |

TABLE 1-continued

Pharmacokinetic parameters (mean ± SD) of bromide after intravenous and per oral administration to eight sheep at a dose of 120 mg/kg.

| Pharmacokinetic variable | Intravenous administration (mean ± SD) | Oral administration (mean ± SD) |
|---|---|---|
| Cl (mL/h/kg) | 0.836 ± 0.255 | — |
| $V_d$ (L/kg) | 0.286 ± 0.031 | — |
| $V_z$ (L/kg) | 0.393 ± 0.102 | 0.388 ± 0.037 |
| $t_{1/2}$ (h) | 387.93 ± 115.35 | 346.72 ± 94.05 |
| F | — | 0.92 |

$C_{max}$, maximum concentration;
$T_{max}$, time of maximum concentration;
$AUC_{0-\infty}$, area under the curve;
$MRT_{0-\infty}$, mean residence time;
Cl, clearance;
$V_d$, volume of distribution,
$V_z$, volume of distribution at pseudo-equilibrium;
$t_{1/2}$, terminal elimination half-life;
F, oral bioavailability.

Figure 6:
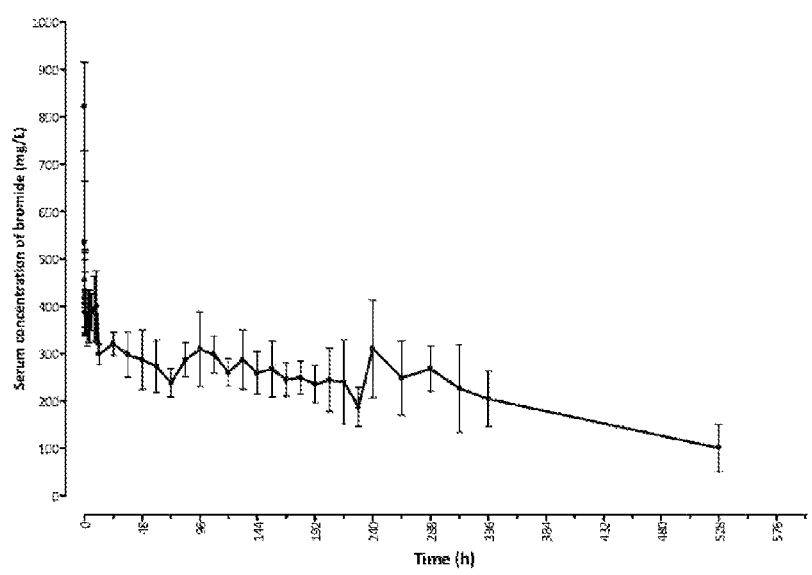
FIG. 6. Serum concentrations (mean±SD) of bromide after intravenous administration to eight sheep at a dose of 120 mg/kg.
Figure 7:
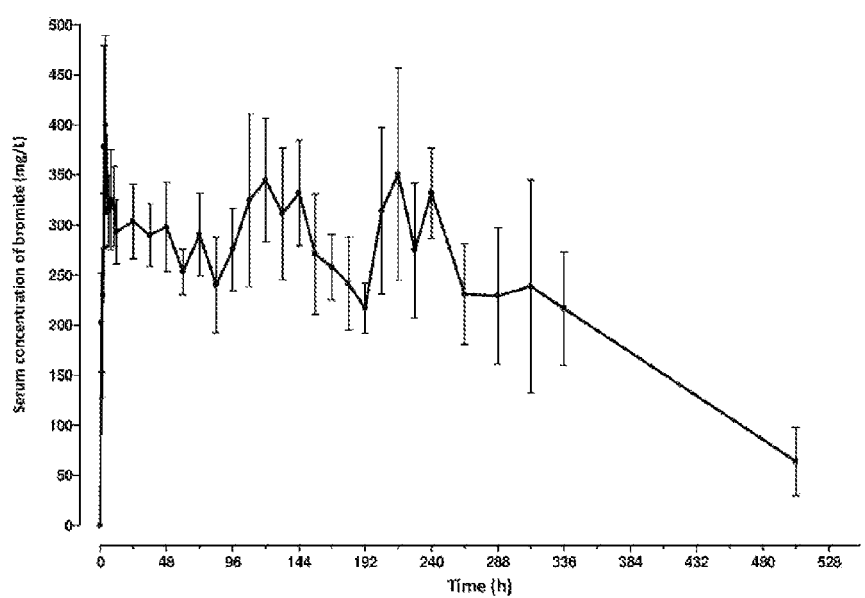
FIG. 7. Serum concentrations (mean±SD) of bromide after oral administration to eight sheep at a dose of 120 mg/kg. Note multiple peaks occurring after 24 hours.

The concentration-time profiles for IV and PO serum bromide are shown in FIGS. 6 and 7, respectively.

The $t_{1/2}$, of Br in sheep following PO administration was 14.4 d, the IV $t_{1/2}$ was 16.2 d; however, the difference between groups was not statistically significant (T=0.7832, df=14, p=0.4466). Because of the long t % following PO administration, the serum Br concentration fluctuated within a narrow range (approximately 200-400 mg/L) for 14 d. This long $t_{1/2}$, with two fold difference between peak and trough values over a two week period indicates that bromide would be useful for prophylactic use.

Figure 2:
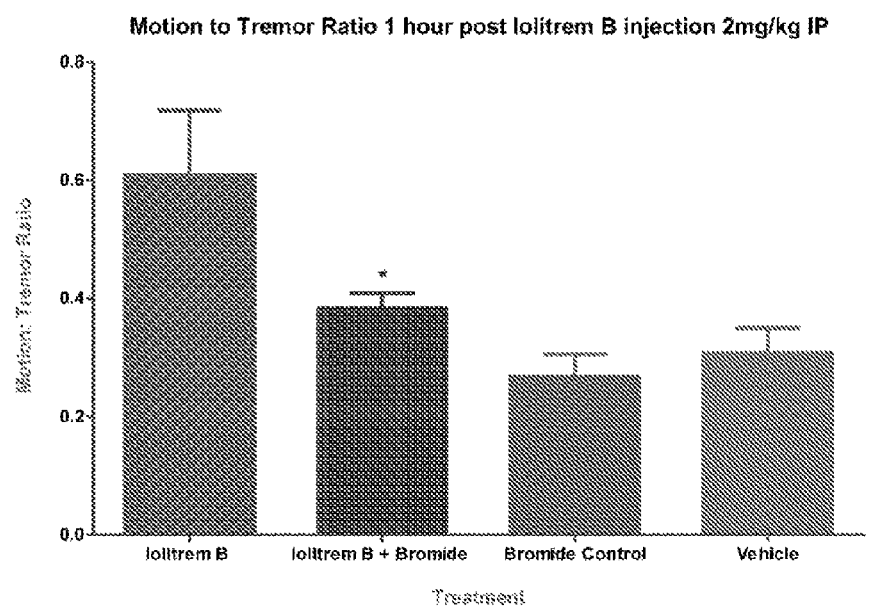
FIG. 2. Ratio of power output from tremor (9-20 Hz range) as compared to total power output (motion:tremor ratio) in lolitrem B treated animals.
Figure 3:
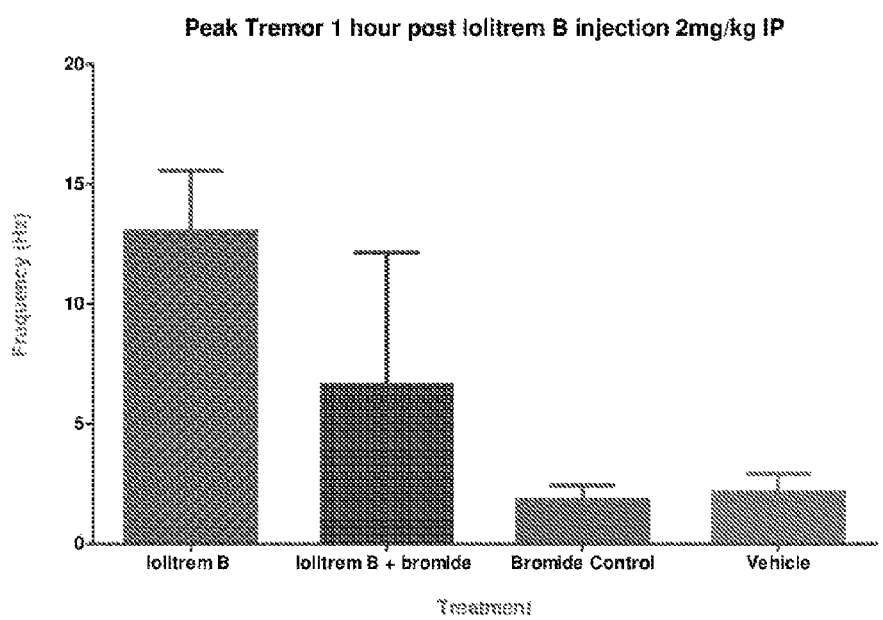
FIG. 3. Peak tremor frequency one hour post lolitrem B injection.
Figure 4:
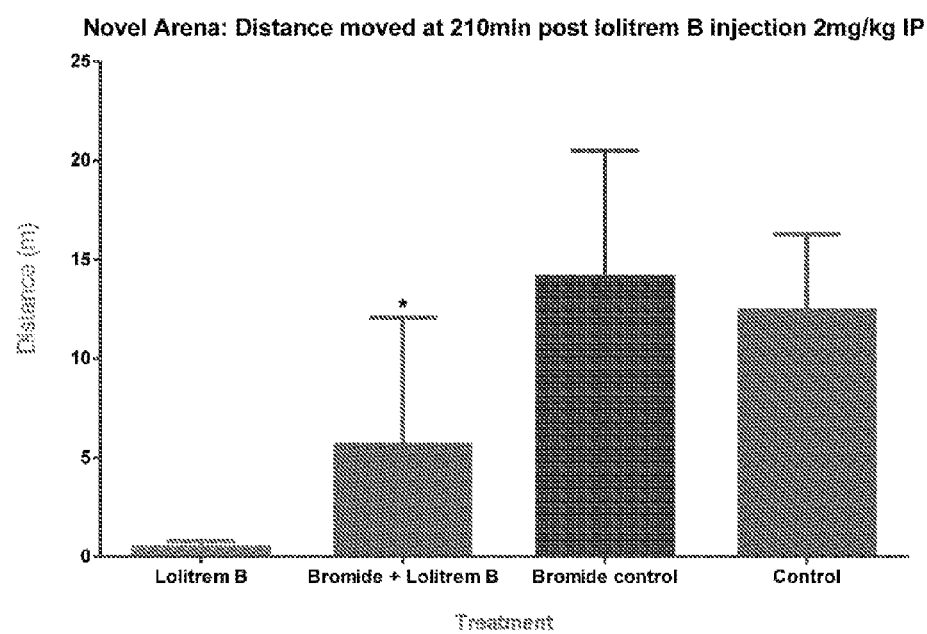
FIG. 4. Distance traveled in animals treated with lolitrem B toxin with or without potassium bromide pre-treatment. Novel arena test: Distance moved 3.5 hours post lolitrem B injection 2 mg/kg IP.
Figure 5:
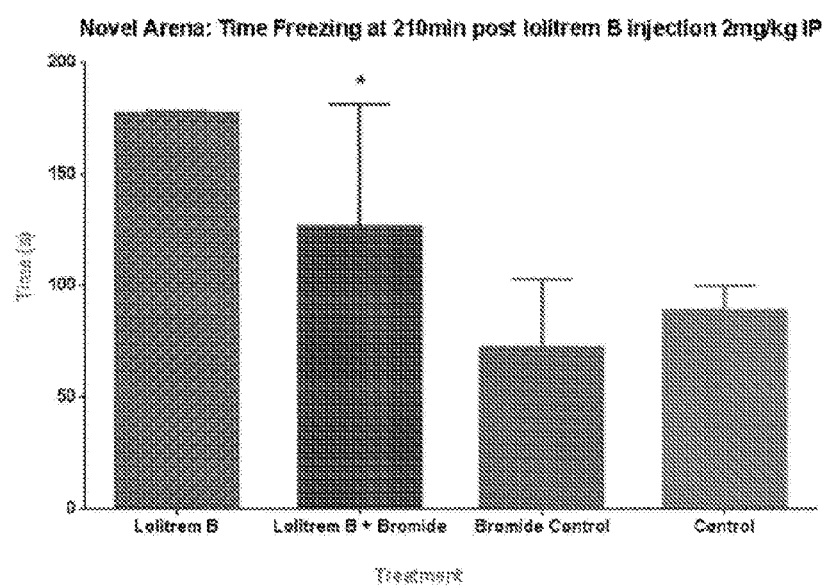
FIG. 5. Freezing episodes in animals treated with lolitrem B toxin with or without potassium bromide pre-treatment. Novel arena test: Freezing time 3.5 hours post lolitrem B injection 2 mg/kg IP.

An interesting finding in this study was the numerous pronounced peaks in the PO concentration versus time curve following the initial absorption phase. These peaks approached the $C_{max}$ seen on day one, but occurred many days later (FIG. 2). Indeed, some sheep had $T_{max}$ values well beyond the initial PO absorption phase. Similar although smaller peaks were also seen with IV Br (FIG. 6).

The mean bioavailability of Br in this trial was 92%, which is desirably high.

The $V_d$ value of 0 286±0.031 reflects the ECF space (although volume of distribution figures are not primary measures of physiological compartments, they do often correlate well). The calculated volume of distribution at pseudo-equilibrium ($V_z$), when equilibration with rumen fluid is assumed, was 0.393±0.102 and 0.388±0.037 L/kg for IV and PO administration, respectively. That these measures are similar is unsurprising as $V_z$ is a proportionality factor relating to concentrations during the log-linear phase of drug elimination, from which $t_{1/2}$ is derived.

Volume of distribution is the parameter used to calculate a loading dose (LD), using the equation LD=V*$C_{ss}$, where $C_{ss}$ is concentration steady state, or the effective concentration for a particular use (as determined by PD studies). The $V_d$ value is most appropriate where bromide is to be given as a PO bolus, and $V_z$ in circumstances where it is to be given over a few days.

When administered PO, bromide in sheep has a long half-life ($t_{1/2}$) of approximately 14 days, with good bioavailability.

Example 4

Summary

Potassium bromide as a treatment for PRGT in sheep was evaluated using two delivery methods: 1) a single dose for treatment of acute staggers and 2) a prophylactic application delivered prior to onset of neurological signs.

On entry to the trial all animals were given a full clinical examination including full neurological examination which included proprioceptive testing, pupillary light reflex, menace reflex, eye position and movement and general cranial nerve function tests. Venous bloods samples were taken for clinical pathology, urine for specific gravity (USG) and electromyography for determination of normal/abnormal muscle activity. Body weight was recorded and heart rate, respiration rate and rectal temperature were recorded daily throughout the period of the trial.

Animals were exposed to a controlled diet containing 0.16 mg/kg body weight (BW) lolitrem B toxin rising to 0.27 mg/kg BW after 21 days exposure to toxic feed. Toxin was delivered as perennial rye grass seed (GA66 AR98, Grasslanz Technology Ltd, NZ) containing very high levels of lolitrem B toxin (11 ppm DM) as a component of the animal's feed intake.

Five treatment groups were established: a control group fed no toxic feed; a positive control group fed toxic feed but given no treatment; an acute treatment group fed toxic feed and administered a single dose of potassium bromide on first day of falling; a prophylactic treatment group fed both potassium bromide daily plus toxic feed for 22 days and a treatment only group given no toxic feed but delivered the prophylactic dose of potassium bromide.

Clinical signs were observed in all three toxic feed groups. The first observable signs of lolitrem B toxicity were a wide based stance, fine tremor of the head and neck and ventral eye deviation (strabismus). Intoxicated animals also exhibited a heightened state of nervousness showing increased reactivity to noise, touch or movement. Intention tremor became increasingly marked as toxicoses proceeded. After approximately 10 days, Type I movement disorders were noted in both positive control and acute treatment animals being defined as an impaired alternating movement (dyscliadochokinesia), bunny-hopping gait and failure to maintain an appropriate direction. This progressed over a period of days to Type 2 movement disorder (Combs, Rendell et al. 2014) defined by increasing rigidity of limbs on forced movement resulting finally in tonic fore and hindlimb extension with the animal collapsing into sternal or lateral recumbency (Combs, Rendell et al. 2014). Type 2 animals were able to recover and regain standing after a short period of time but would commonly fall if encouraged to move again. Identification of Type 2 movement disorder and day of falling was determined to be the date for entry to treatment for the acute treatment group. Time to falling was recorded for all animals and ranged from immediate upon encouragement to move to approximately 90 seconds after encouragement to move. On neurological examination, intoxicated animals were found to have a normal pupillary light reflex but reduced or absent menace response with involuntary eye movements (nystagmus) of increased amplitude.

On day of falling, acute treatment animals were given an oral dose of 300 mg/kg BW of potassium bromide. Movement, neurological signs and general clinical signs were examined 24 and 48 hours after treatment at which point animals were euthanased for full post mortem. Treatment with potassium bromide was observed to significantly improve time to falling in intoxicated animals with most (8/9) animals failing to fall when driven to movement for a continuous period of 5 minutes. Positive control animals, which had not been treated with potassium bromide, showed no improvement over the same time period (7/7 falling).

Clinical pathological analysis of serum from all treatment groups showed no significant difference in any biochemical markers associated with liver function. Renal function was observed to be mildly compromised in toxin only and acute treatment groups with mild elevations in creatinine and urea observed but not outside normal ranges for our cohort. USG was also marginally increased compared to reference ranges. Although not considered to be clinically significant in these animals it does demonstrate increasing fluid losses and/or decreasing fluid intake in intoxicated animals; this is likely to be of greater clinical importance in the field where animals can be under heat and nutritional stress.

Early pathological lesions were noted in the brain of intoxicated animals; these included small numbers of spheroids located in the granule cell layer, mainly in the lateral cerebellum, as well as pyknotic granule cell nuclei and occasional vacuolated Purkinje neurons. These changes represent the earliest lesions of PRGT reported.

Animals in the potassium bromide prophylactic group also showed improved movement with treatment with only one in this treatment group progressing to falling in the designated 22 days of treatment compared to 5 animals in Groups 2 and 3 over the same timeframe. Animals in this group showed other neurological signs similar to their toxin only counterparts.

The data presented from this study confirm potassium bromide as an effective therapy and prophylactic agent for neurological PRGT, or "Rye Grass Staggers.

Methodology 1.1 Animals

Animals were White Sussex×Merino first cross male lambs of between 10-12 months of age (n=45, live weight 36.1±3.02 kg) sourced from a single producer. They had been maintained under normal husbandry conditions grazing mixed lucerne and wheat stubble pastures prior to entry to the trial. No animals used exhibited any obvious pre-existing pathology. Animals were allowed to acclimatise to the animal house for 7 days prior to entry to the trial. During this period they were fed a restricted diet of lucerne chaff, approximately 2.5% live weight, and had access to water ad libitum.

1.2 Toxic Feed

To generate a feed containing toxic levels of lolitrem B without confounding high levels of ergovaline, a novel endophyte-infested perennial rye grass seed (Ga66 AR98, Grasslanz technology Ltd, New Zealand) was sourced. Toxin analysis by LCMS was carried out by AgResearch, New Zealand, which showed the seed to contain 11.1 mg/kg DM lolitrem B toxin. No ergovalline was detected.

On entry to the trial, all animals receiving toxic feed were exposed to a diet containing experimental ryegrass seed with a final lolitrem B concentration of 0.08 mg/kg LW, lucerne chaff and molasses 30% w/v for 3 days. After this induction period, the toxin content of the feed was increased to 0.16 mg/kg LW for the duration of the trial. For any animal that had not showed Type 2 movement disorder at 21 days, the dose was increased to 0.27 mg/kg LW until falling. Ryegrass seed constituted up to 65% of available Feed on Offer (FOO) by dry weight contributing a metabolisable energy of 12.1 Mj/kg DM.

1.3 Physiological Monitoring

At entry to the trial, all animals were subjected to a full clinical examination. Live weight was recorded. Venous blood and urine samples were collected for laboratory. Animals were also subjected to gait analysis, neurological examination including proprioceptive testing, cranial nerve examination and papillary light and menace reflexes. Electromyography (EMG) of tricep and neck muscles was performed. Gait analysis (see below) was repeated at three day intervals until onset of significant clinical signs and/or gait abnormality at which point animals were subjected to gait analysis daily. Gait analysis was recorded on video each occasion.

General clinical signs were also noted on a daily basis; these included observations of nervousness or agitation, changes in normal placement of body, limb or head position changes in faecal consistency, feeding behaviour or water consumption, observeable tremor of the body or head, eye position (strabismus) and movement (nystagmus), locomotory disturbances, or any other clinical changes worthy of note. Feed and water intake was monitored daily for the duration of the trial. Heart rate, respiration rate at rest and rectal temperature were also monitored daily.

1.4 Treatments 1.4.1. Treatment Rates for Potassium Bromide

The anticonvulsant range of bromide in monogastric species is 0.8 to 20 mg/mL (Podell and Fenner 1993). As such, the lower bound of the monogastric anticonvulsant range was initially used as the target blood concentration in sheep. Using the equation Loading Dose (LD)=V*target concentration, and factoring in the 92% oral bioavailability of bromide in sheep, a LD of 340 mg/kg was obtained as an acute treatment.

Prophylactic sheep received a split loading dose of 300 mg/kg on day 1, 120 mg/kg (100 mg LD+20 mg/kg daily maintenance dose) on day 2, 120 mg/kg on day 3 and 20 mg/kg daily for the duration of the trial. An acute treatment dose of 300 mg/kg LW was used for the trial. Both prophylactic and acute treatment doses were envisaged to give serum concentrations of 750 to 1000 μg/ml for the duration of the initial weeks of the trial.

1.4.2. Establishment of Treatment Groups

There were five treatment groups:

Group 1—Negative Control: lucerne chaff only;

Group 2—Positive Control: lucerne chaff containing 0.16 mg/kg LW lolitrem B;

Group 3—Acute potassium bromide (KBr) treatment: lucerne chaff containing 0.16 mg/kg LW lolitrem B, treated orally with 300 mg/kg bromide (Sigma Aldrich) on day of falling;

Group 4—Prophylactic Or treatment: lucerne chaff containing 0.16 mg/kg LW lolitrem B, treated orally with a prophylactic therapeutic dose of potassium bromide with a loading dose give over 72 hours on entry to the trial with a continued maintenance dose administered orally daily (see below);

Group 5—Prophylactic KBr treatment control: lucerne chaff only, treated orally with prophylactic potassium bromide as described below.

Prophylactic treatment sheep (Groups 4 & 5) received a split loading dose of 300 mg/kg on day 1 of the trial, 120 mg/kg (100 mg LD 20 mg/kg daily maintenance dose) on day 2, 120 mg/kg on day 3 and 20 mg/kg daily thereafter. Acute therapy sheep were dosed with a single dose of 300 mg/kg on day of falling.

Animals entered the trial in cohorts of five, each cohort containing one animal from each treatment group with entry occurring over three consecutive days such that groups of 15 animals undertook the trial together. Three sets of 15 animals were used for this study (n=45) with each treatment group containing nine animals. Animals were maintained on the treatments as described above for the duration of the trial period.

End of the trial was defined for Groups 2 and 3 as date of falling. Group 1 animals entered the end of trial protocol with their Group 2 counterparts. Group 4 and 5 animals entered the end of trial protocol after 22 days. This end of trial protocol consisted of the following analysis:
- On Day 1: animals were subjected to a full clinical examination, gait analysis, urine and blood collection, neurological examination and EMG.
- On Day 2: further gait analysis was recorded,
- On Day 3: animals were again subjected to full clinical examination, gait analysis, urine and blood collection, neurological examination and EMG as well as live weight recorded prior to necropsy.

1.5. Electromyography

EMGs were recorded on entry to the trial, entry to the end of trial (Day 1) and date of post mortem (Day 3) using Powerlab™ (ADInstruments, Castle Hill, Australia) and data recorded using LabChart™ software (ADInstruments, Australia). In preparation, the fleece was shorn from an area over the triceps muscle and along brachiocephalicus muscle of the neck. EMG electrodes were attached to the skin using SuperGlue™. Muscle activity was recorded for a minimum of three minutes with the animal standing at rest with a band pass filter set at 100 Hz. Three minute EMG recordings were taken using Ag—AgCl surface electrodes over the triceps muscle on to entry to the trial, on first day of falling (Day 1) and 48 hours post treatment (Day 3). Data analysis was achieved by application of a Fast-Fourier transformation for statistical comparison. Area under the curve was then calculated at frequencies between 5 and 30 Hz to estimate tremor intensity.

1.6. Gait Analysis

Gait analysis was performed on entry to the trial and at designated time points throughout the trial as described above. To achieve this, animals were moved from their individual pens to an external yard in their cohort groups (five animals, one from each treatment). Animals were then encouraged to move at a run, initially in a group and then individually, for a minimum of three minutes per animal whilst their movement was captured on video and gait observations recorded.

Once all animals had been analysed the whole cohort was returned to their individual pens. Gait abnormalities such as stumbling, falling or disorientation were noted, including observation of Type 1 or Type 2 gait changes as described in Combs et, al., (2014). Type I movement disorder is defined as an impaired alternating movement (dysdiadochokinesia), bunny-hopping gait and failure to maintain an appropriate direction. Type 2 movement disorder is defined by increasing rigidity of limbs on forced movement resulting finally in tonic fore and hind limb extension with the animal collapsing into sternal or lateral recumbency (Combs, Rendell et at 2014). Scores between those denoted above were considered as a gradation between the stated clinical observations. Analysis of gait was performed using the following scale in Table 2 and a composite score noted for each animal for each day during the end of trial protocol. A total score out of 30 was determined for each animal. The higher the score the greater the locomotory disturbance. Time to falling was determined post trial by analysis of video material,

TABLE 2

Gait analysis, scale of clinical observations.

| Clinical observation | Score 1 | Score 3 | Score 5 |
|---|---|---|---|
| Dysdiadochokinesis | Mild disunited fore/hind limb coordination on acceleration | Changes in forelimb/hindlimb coordination such as pacing at moderate pace or gait | Continuous bunny-hopping gait |
| Myoclonus | Mild limb rigidity (hind > fore) | Increased severity, significant forelimb involvement | Severe-all four limbs involved with characteristic arching |
| Directional movement | Reduce ability to change direction | Frequently moves in abnormal direction (i.e. near misses with stationary objects) | Unable to control or maintain direction (frequently hits stationary objects) |
| Ataxia | Mild-wide based gait only | Body rolling, wide based gait | Body rolling and frequent limb crossing |
| Failure to maintain ambulation | Stumbling without falling on rapid movement | Frequent stumbling without falling | Falling |
| Clonic seizures | | | Seizures |

1.7. Laboratory Analysis

Venous blood samples collected for biochemical analysis and haematocrit (PCV), and urine for USG, at three specific time points during the experiment for all animals: 1) on entry to the trial; 2) on date of entry to the end of trial protocol and, 3) on day of necropsy. Additional venous blood samples were occasionally collected for analysis of serum bromide (see below).

For venous sampling, blood was collected from either the right or left jugular vein as determined by convenience and sampler preference. Needle hubs and sterile, single use 21 G needles and 10 mL Vacutainer® tubes were used for collection. Two Vacutainer® tube types were used for each animal: one containing a clot activator for serum collection, the other contained ethylenediamine tetra-acetic acid (EDTA) to prevent clotting. Tubes were inverted repetitively immediately after collection prior to storage on ice for transport to the laboratory. EDTA tubes were kept chilled until processing. Serum blood tubes were allowed to clot for at least 30 minutes before serum separation by centrifugation at 1000 rpm for 10 minutes. All samples were transported and processed within 60 minutes of collection.

Urine samples were collected by attachment of a clean plastic bag using SuperGlue™ to the fleece on either side of the preputial opening. The bag was removed as soon as urine collection had been achieved and samples transferred to a clean plastic container. Samples were stored at 4° C. prior to removal to the laboratory for processing. Urine specific gravity (USG) was determined using a refractometer (VQ5600 refractometer, VetQuip, Australia).

Haematological and biochemical analysis was performed by the laboratory within 60 minutes of blood collection. Haematological analytes were measured using a CellDyn 3700 Haematology System (Abbott Diagnostics, Abbott Park, Ill., USA). Biochemical analysis was performed using a Konelab 30i clinical chemistry analyser (Thermo Electro Corp., Vantaa, Finland), using reagents from Thermo Scientific. See Appendix 1 for a full list of haematological analytes reported.

1.8. Necropsy

A full clinical examination was performed prior to euthanasia. At euthanasia, 100 I.U. heparin (Provet Riverina Pty Ltd) was injected into the jugular vein, followed shortly by Lethabarb (20 mL/40 kg LW). Immediately after euthanasia, the ventral articulation of C1 was exposed and cerebrospinal fluid (CSF) collected using a 23 g needle. The head was then removed and subjected to perfusion fixation. Briefly, the carotid arteries were exposed and a small catheter inserted and ligated to secure the perfusion lines. Two liters of 0.1% phosphate buffered saline (PBS) containing 3000 I.U of heparin/L was then slowly perfused via the ligated vessels at a pressure of 90 mm Hg using a Microgon peristaltic Pump (Microgon, Laguna Hills, Calif.). Once complete this was replaced with 4% paraformaldehyde (Sigma-Alrich) in 0.1% PBS and a further two liters allowed to perfuse slowly through the tissues of the head. Once complete, catheters were removed and the whole head placed at 4° C. overnight to complete fixation. Twenty-four hours post perfusion fixation the brain was removed from the skull and placed in 10% formal saline for storage until dissection for processing to wax sections.

Concurrent to fixation perfusion of the head, a routine ovine necropsy was performed and all general tissues taken for routine histopathology. These were heart, lung, oesophagus and trachea, liver, spleen, gut (rumen, abomasum, ileocaecal junction, ileum, caecum and colon), skeletal muscle (gluteal, tricep and diaphram), kidney, pancreas, thymus, ileal and cranial lymph nodes as well as tissues from any gross abnormalities observed at time post necropsy. Other samples: subcutaneous fat, renal fat, gluteal muscle, kidney, faeces and rumen contents were collected and stored at −80° C. for future toxicological analysis. Samples for routine histopathology were fixed in 10% formal saline for a minimum of 48 hours before processing to wax using an automated wax embedder (Shandon Excelsior ES Tissue Processor, Thermo Fisher Scientific).

For histopathology, sections of brain and spinal cord included the following regions: mid cerebellar peduncle; mid and lateral sections of cerebellum; obex, occipital cortex; rostral colliculi; basal ganglia; frontal cortex; temporal cortex; thalamus; hippocampus; internal capsule; cervical, thoracic and lumbar spinal cord and pituitary. Other tissues examined for routine histopathology were kidney; lung; ileum; heart; liver including, gall bladder and bile duct; diaphragm; rumen; and colon. All sections were cut at 5 µm and stained with Haematoxylin and Eosin (H&E) using an automated staining system (Shandon Varistain Gemini ES Slide Stainer, Thermo Fisher Scientific).

1.9. Analysis of Serum and Cerebrospinal Bromide Concentrations.

Serum bromide concentrations were determined by calorimetric spectrophotometry as previously described (Tietz 1976), with some modification. Briefly, 0.5 mL of serum was added to 4.5 mL of 10% trichloroacetic acid (Sigma-Aldrich) in a 10 mL centrifuge tube, vortexed, then centrifuged for 15 min at 2000 g. 2.5 mL of supernatant was then mixed with 0.25 mL of 0.5% $Au_2Cl_6$ (Sigma-Aldrich) and left to stand for 30 min. Absorbance was measured with a spectrophotometer at 440 nm. The standard curve was linear in the range of 25 µg/mL to 5000 µg/mL, $R^2=09992$. The lower limit of quantification (LOQ) was 25 µg/mL.

1.10. Statistical Analysis

Reference intervals were defined as the interval containing the central 95% of data obtained for each analyte after the exclusion of outliers. Outliers were excluded based on the method proposed by Dixon (Dixon 1953), and modified by Reed, Henry & Mason (Reed 1971). Distributions of the outlier-excluded values were tested for normality using the Kolmogorov-Smirnov test using IBM SPSS™, Version 20.0.0. A Kolmogorov-Smirnov value >0.050 was the criterion for describing the data as a normal distribution. For analysis of biochemical data, a standard liner regression model was used where model assumptions were met. Spearmann or Kendall's correlation analysis was used for all other data sets.

Results

1. Establishment of an Experimental Model of 'Rye Grass Staggers' in Sheep

Clinical signs attributable to PRGT in field cases vary in their description. Generally the syndrome has been characterised by neurological changes such as head shaking, ill-coordination, staggering and collapse (Cheeke 1995) with spinovestibular cerebellar signs noted including eye deviation (Mayhew 2009). The movement disorder associated with 'ryegrass staggers' represents a specific sequence of dyskinesis (Combs, Rendell et al. 2014). To determine establishment of a comparable clinical syndrome to that observed in field cases of perennial rye grass toxicosis, detailed neurological observations and gait analysis were performed systematically throughout the trial to define the earliest observable neurological signs as well as progression from no movement disorder, to Type 1 and Type 2 gait changes as defined by Combs et al. (2014) (see Section 2.6).

2. Time to Onset and Clinical Signs Associated with Experimental Lolitrem B Toxicosis Neurological signs of lolitrem B intoxication followed a clear progression. The first observable clinical signs were a fine tremor of the head and neck, ataxia presenting as an alteration in stance or limb placement at rest which generally coincided with onset of Type 1 gait changes. Ventral strabismus was also observed in a proportion of intoxicated animals affecting 9/9 animals in Group 2, 7/9 in Group 3 and 6 (animals in Group 4). Type 2 gait changes followed Type 1 approximately 9 days later with a range of between 1 and 27 days. Observations of Type 2 gait changes were usually coincident within 4 days of falling. Menace reflex was either lost or reduced in lolitrem B intoxicated animals but their pupillary light reflex was normal.

TABLE 3

Clinical signs associated with ingestion of lolitrem B-containing toxic feed and treatment.

| Group | Mean number of days to onset (+/−s.e.m.) Number of animals affected | | | |
|---|---|---|---|---|
| | First clinical signs | Fine tremor | Altered stance | Major body clonus |
| Group 1- Control | 0 0/9 | 0 0/9 | 0 0/9 | 0 0/9 |
| Group 2- Toxin only | 7.56(+/−2.06) 9/9 | 8.22(+/−2.58) 9/9 | 11.78(+/−2.58) 9/9 | 17.33(+/−3.51) 3/9 |
| Group 3- Toxin KBr Acute Txt | 8.56(+/−1.94) 9/9 | 12.43(+/−4.82) 7/9 | 10.22(+/−2.10) 9/9 | 11.67(+/−2.88) 3/9 |
| Group 4- Toxin KBr Proph Txt | 6.33(+/−1.73) 9/9[a] | 12.14(+/−4.45) 7/9 | 8.33(+/−1.22) 9/9 | 10.67(+/−2.65) 5/9 |
| Group 5- KBr Proph Txt | 10.75(+/−4.46) 8/9[b] | 11.00(+/−0.0) 1/9 | 11.0(+/−4.69) 4/9 | 0 0/9 |

[a]Includes 4/9 animals showing evidence of mild anxiolysis
[b]Includes 5/9 animals showing evidence of mild anxiolysis This pattern represented a clear progression of disease:
Early clinical signs: mild tremor of the head and neck, ventral strabismus, abnormal body stance at rest, increased reactivity;
Intermediate clinical signs: Type 1 movement disorder, stumbling usually of forelimbs, gross limb and/or body tremor, inappropriate decision making regarding direction, increased reactivity to noise movement, ventral strabismus;
Advanced clinical signs: Type 2 movement disorder, inability to follow a direction of movement for an extended period, stumbling and falling, collision with objects, collapse into sterna or lateral recumbency, generalise myoclonus, limb extension and opisthotonos, significant altered body stance at rest, heightened reactivity to noise/movement, loss of menace reflex.

Figure 8:
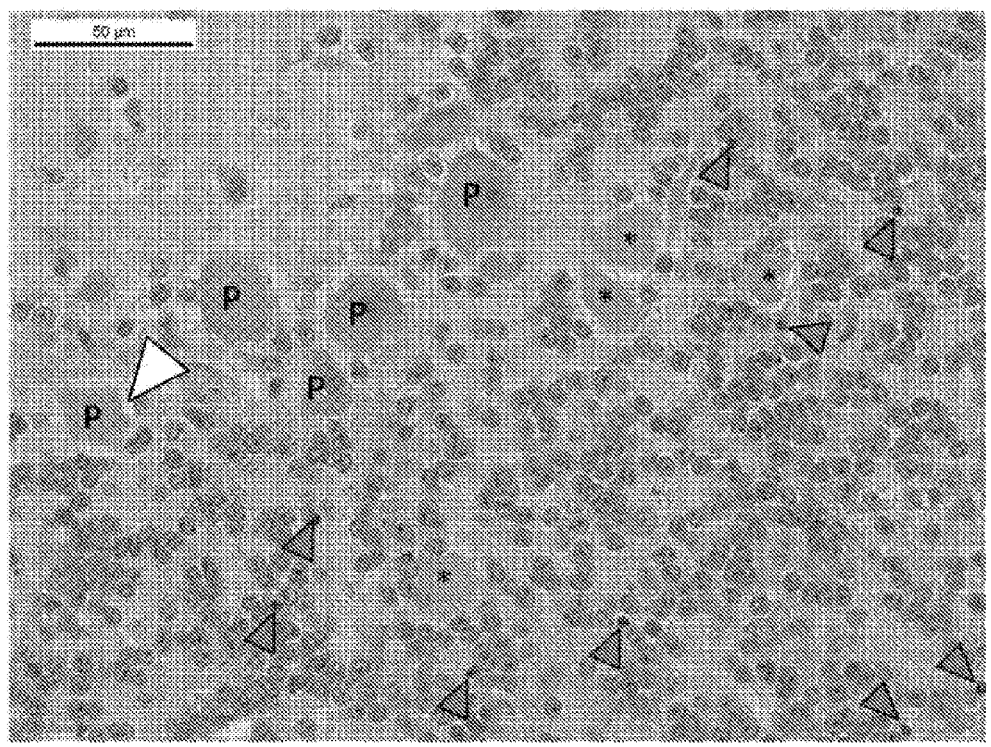
FIG. 8. Histological lesions observed in the cerebellum of animals intoxicated with lolitrem B. Three clear histopathological lesions are noted: spheroids (*) and pyknotic nuclei (red arrowheads) present in the granular later and vacuolation within Purkinje neurons (white arrow head).

Histopathological changes at necropsy mimicked those observed in field cases (Parton K 2006, Combs, Rendell et al. 2014) with some additional features (see FIG. 8). Lesions were restricted to the cerebellum and consisted of three specific histological features:
1) spheroids (axonal swellings) located in the granule cell layer;
2) presence of pyknotic granule cell neurons in the granular layer and less frequently,
3) interneuronal vacuolation of Purkinje Neuron cell bodies.

Spheroids were observed to be present in the molecular layer of the cerebellum but these may be incidental to those observed in the granular layer and/or represent a background lesion. Intraneuronal vacuolation of Purkinje neurons is likely to represent the earliest neuropathologal changes in this cell type. Formation of spheroids, in the absence of other notable pathology, is commonly reported as a 'diagnostic' lesion in field cases of PRGT.

Lesions were observed in the highest number in those animals exposed to lolitrem B toxin only (Group 2, Table 3) with 7/9 animals presenting in the granular layer with spheroids and 9/9 exhibiting pyknotic cell bodies. A similar pattern was observed in the other two toxin treated groups (Groups 3 & 4, Table 4). In all toxin treated groups, spheroids and pyknotic cell bodies in the granular layer were the most common finding. A lower incidence of spheroids in the molecular layer was noted, the incidence included both the prophylactic treatment only group (Group 5) and control group (Group 1) suggesting that this may be an incidental finding in these cases (see Table 4).

TABLE 4

Acute histopathological lesions of the cerebellum associated with ingestion of lolitrem B-containing toxic feed and treatment with either acute or prophylactic potassium bromide (KBr).

| | Incidence | | | |
|---|---|---|---|---|
| | Spheroids | | Purkinje neuron vacuolation | Pyknotic cell bodies in granular layer |
| Group | Molecular layer | Granular layer | | |
| 1 | 1/9 | 0/9 | 1/9 | 0/9 |
| 2 | 1/9 | 7/9 | 5/9 | 9/9 |
| 3 | 0/9 | 7/9 | 2/9 | 5/9 |
| 4 | 3/9 | 6/9 | 1/9 | 9/9 |
| 5 | 3/9 | 1/9 | 0/9 | 2/9 |

Abbreviation:
PN, Purkinje neuron.
Key to groups:
1: no toxin, no treatment control;
2: toxin only;
3: toxin plus acute treatment;
4: toxin plus prophylactic treatment;
5: prophylactic treatment only.

Pyknotic nuclei, indicative of cell death in the granular layer of the cerebellum have not been previously reported in field cases of PRGT. This suggests that these are acute lesions or have been overlooked in previous investigations due to lack or 'normal' control animals for comparison. No other lesions were found in any other area of the brain examined.

One animal in the non-toxin, no treatment control group (Group 1) presented at post mortem with multifocal gliosis affecting the basal ganglia had been noted has having an observable albeit mild movement abnormality during the trial. This animal represents a background lesion in this group and was excluded from any further analysis.

Incidental pathological findings, considered to be irrelevant to the experiment, included some systemic changes: notably mild lymphocytic cholangeohepatitis (animals 7 & 9, Group 4; animals 8 & 9, Group 5); mild lymphocytic hepatitis (animals 2 & 4, Group 1; animal 1, Group 5); mild lymphycytic pyelitis (animal 2, Group 1; animal 3, Group 2; animal 3, Group 3 and animals 7 & 9 Group 5); mild interstitial nephritis (animal 3, Group 1; animals 5 & 6 Group 2; animal 5, Group 5); mild tubular nephropathy (animal 9, group 5); bronchopneumonia and pleuritis (animal 7, Group 5); mild lymphocytic colitis (animal 7, Group 3) and lymphadenitis (animal 2, Group 5). Multifocal myositis and multifocal lymphycytic myocarditis was observed in all animals secondary to presence of sarcosysts. Again, these are suggested to be incidental background lesions identified due to the size of the cohort.

3. Treatment with a Single Acute Dose of Oral Potassium Bromide Decreases Severity of Tremor, Increases Time to Falling and Improves Gait in Lolitrem B Intoxicated Animals Animals that met the entry criteria (severe Type 2 gait abnormality and falling) were submitted to the end-of-trial protocol. This consisted of acute treatment with 300 mg/kg potassium bromide orally; three days of testing, starting on date of falling, with necropsy on Day 3. Animals were subjected to the following tests on days 1 and 3: gait analysis, full neurological examination, venous blood and urine sampling and EMG. Only gait analysis was performed on day 2.

Figure 9:
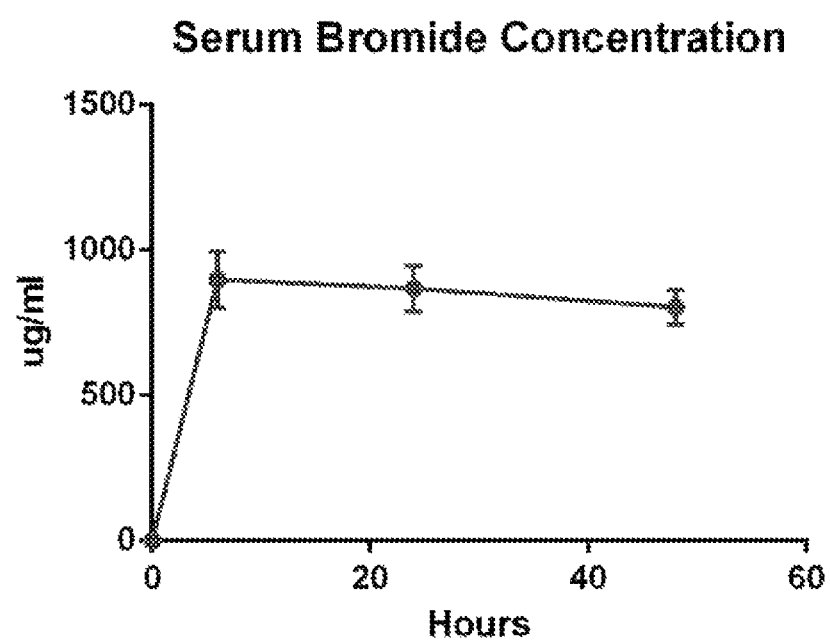
FIG. 9. Serum concentrations in lolitrem B-intoxicated sheep treated with an acute oral dose of potassium bromide.

Bromide concentration in serum was monitored 6 hours, 24 hours and 48 hours after treatment. Similar to that observed in the pre-trial PK study, serum concentrations rose sharply in the first 6 hours after administration (mean serum concentration 6 hours: 899.43 µg/ml+/−56.44, n=3), falling slightly over the 48 hour treatment period to a final mean serum concentration of 804.34 µg/ml+/−24.26, (n=6) after 48 hours. This analysis indicates that high levels of bioavailability of potassium bromide from 6 hours post treatment (see FIG. 9). This data is supported by PK studies performed prior to this trial in which high levels of bioavailability were also observed with serum bromide levels peaking at 6 hours post administration (Combs and Edwards, personal communication).

Figure 10:
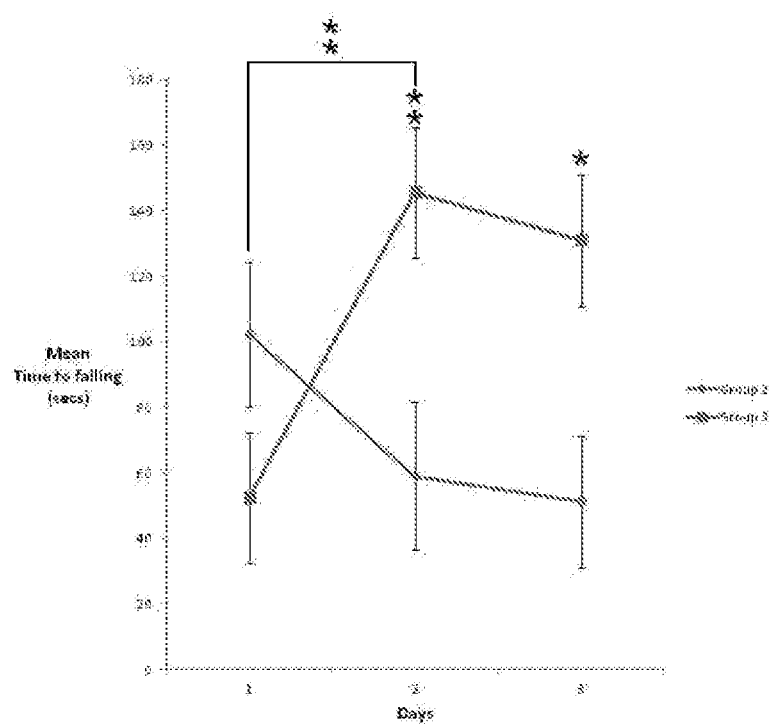
FIG. 10. Time to falling in seconds of animals exposed to lolitrem B toxin only or toxin plus treatment with acute oral potassium bromide. Values shown for Day1 for Group 3 represent time to falling prior to treatment Group 2 (lolitrem B toxin only, n=8) and Group 3 (lolitrem B toxin plus single acute treatment with potassium bromide, n=9). * Significant difference between pre- and post-trial samples, p=<0.05; ** Significant difference between pre- and post-trial samples, p=<0.01.

Animals treated with a single oral dose of bromide 300 mg/kg LW showed significant extension in time to falling 24 hours after treatment (Group 2 day 1: 52.44 seconds±19.55 seconds; Day 2: 145.66±22.07 seconds; students t test; p=0.002, FIG. 10). Although no significant difference was observed between days 2 and 3 within treatment groups, differences between groups on both days were highly significant (Group 2 Day 2: 145.66±22.07 seconds; Group 3 Day 2: 59.0±23.50 seconds; p=0.003; Group 2 Day 3: 124.75±22.06 seconds; Group 3 Day 3: 51.52±20.23 seconds: p=0.02. FIG. 10). This data represents a significant increase in time to falling in Group 3 (toxin plus acute treatment) on days 2 and 3, compared to day 1, whilst a coincident reduction in time to falling is observed in untreated animals (Group 2, toxin only) (FIG. 10). This data suggests improved coordination in the acute treatment group (Group 3) with a deterioration with increasing toxin load over the same timeframe in their untreated counterparts.

Figure 11:
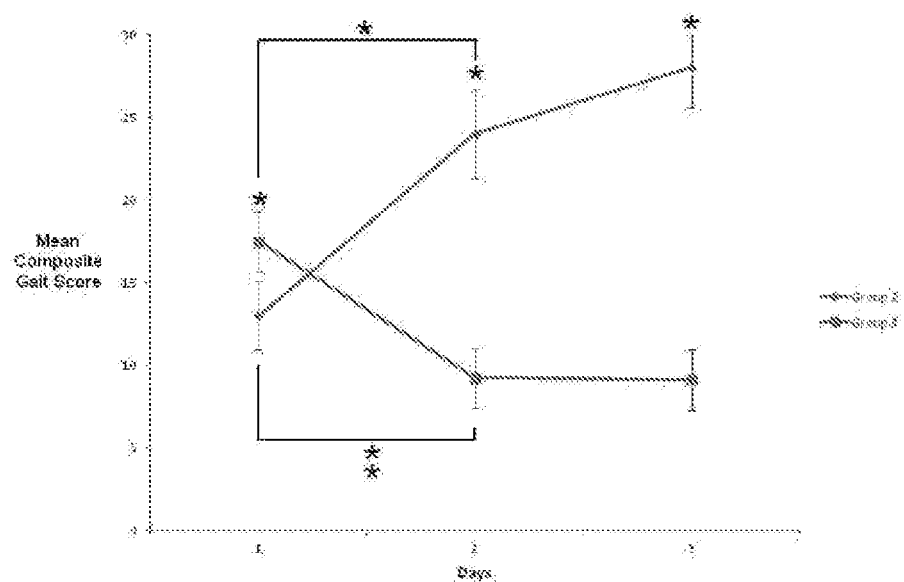
FIG. 11. Mean composite gait score over time for animals exposed to lolitrem B toxin only or toxin plus treatment with acute oral potassium bromide. * Significant difference between pre- and post-trial samples, p=<0.05; ** Significant difference between pre- and post-trial samples, p=<0.01.

Gait analysis showed a similar trend with composite scores decreasing in the potassium bromide acute treatment group (Group 3) indicative of a return to normal gait characteristics on treatment, whilst scores increased over time in their untreated counterparts (see FIG. 11). A significant reduction in composite gait score was observed between Day 1 (pre-treatment) and Day 2 (24 hours post treatment) in Group 3 animals which were exposed to lolitrem B toxin and treated orally with 300 mg/kg LW potassium bromide (p=0.001, FIG. 11). This is consistent with the improvement in maintenance of normal ambulation observed by increased time to falling post treatment (see FIG. 10). Conversely, composite gait scores are observed to increase in untreated intoxicated animals (Group 2) over the same time course (p=0.05) showing a deterioration in gait over time.

Figure 12:
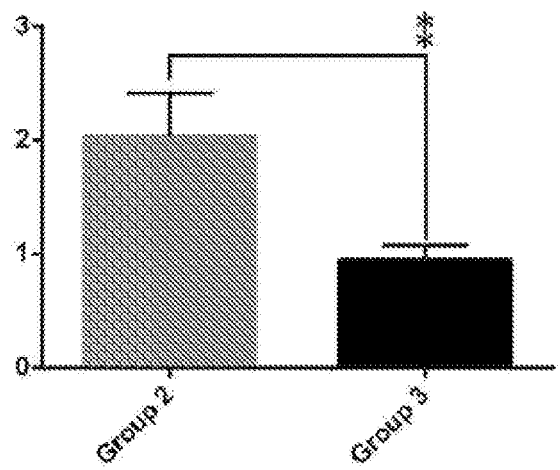
FIG. 12. Median Day 3 tremor intensity ratios for Groups 2 (lolitrem B intoxicated, no treatment) and 3 (lolitrem B intoxicated, acute KBr treatment. ** Significant difference between treated and untreated animals, p=<0.01.

Treatment with potassium bromide was also found to decrease tremor intensity in intoxicated animals, Both Group 2 and Group 3 animals showed significant increases in tremor intensity between pre-trial and Day 1 of testing (p=0.002). Neither group showed a significant difference within groups between Days 1 and 3. However when Day 1: Day 3 tremor intensity ratios are compared between groups there is a significant difference (p=0.01, see FIG. 12). The median ratio for the Group 2 was 2.03 indicating an increasing intensity of tremor whereas in Group 3 the mean ration is 0.81 indicating a stabilisation of the tremor despite increasing intoxication over this time period (FIG. 12).

Figure 13:
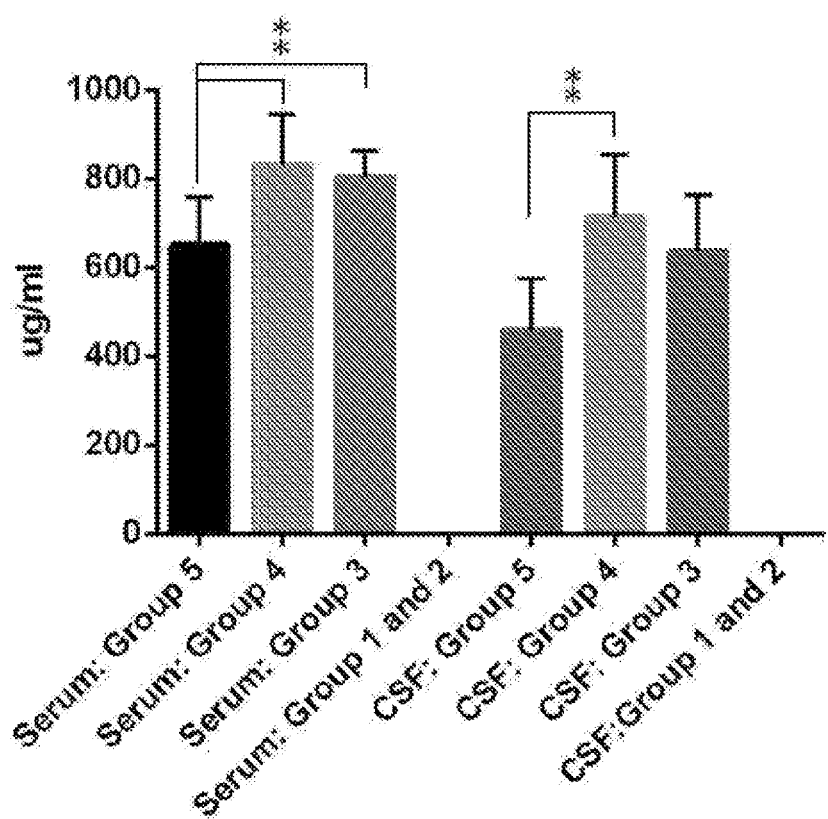
FIG. 13. Bromide levels in serum and CSF are higher in lolitrem B intoxicated animals than in unintoxicated controls. Serum: Group 5, n=7; Group 4, n=7; Group 3 n=5, CSF: Group 5, n=6; Group 5, n=7; Group 3 n=3.

4. Serum and CSF Bromide Levels are Increased in the Presence of Lolitrem B Toxin To determine whether animals were maintaining prophylactic levels of bromide sufficient to be clinically effective after 22 days of administration, serum and CSF bromide concentrations were analysed on day of post mortem for all bromide treatment groups (Group 3: acute treatment 48 hours previously; 4: =bromide prophylactic treatment plus lolitrem B toxin for 22 days, and 5: bromide prophylactic treatment only for 22 days). Serum and CSF concentrations of bromide were found to be significantly higher in the bromide prophylactic treatment plus lolitrem B group (Group 4) than in the prophylactic treatment group 5 alone (see FIG. 13) by a factor of 1.27:1 in serum and 1.57:1 in CSF. Data suggest that animals intoxicated with lolitrem B in this study failed to excrete bromide with the same efficiency as their unintoxicated counterparts thus maintaining higher levels of circulating bromide. The mean ratio of serum bromide:CSF bromide was also considered. This value was 0.74 for bromide prophylactic controls (Group 5); 0.91 for Bromide prophylactic treatment plus lolitrem B animals (Group 4) and 0.81 for acute bromide treatment plus lolitrem B animals (Group 3). This suggests that intoxicated animals treated with bromide might also maintain higher bromide levels in CSF compared to their un-intoxicated counterparts. This observation warrants further investigation as it suggests that very low levels of bromide might still deliver a prophylactic effect in cases of lolitrem B intoxication.

To investigate a possible mechanism for this difference, trace element content of the animal's feed was determined (DPI NWS Environmental Laboratory, Wollongbar, NSW. A very low level of chloride was found to be present in ryegrass seed compared to lucerne chaff (sodium: lucerne, 0.59%; ryegrass seed, 0.086%). Therefore, it is possible that this low level of chloride in the FOO to animals in the bromide prophylactic treatment Group 4 could have contributed to counter-current exchange of bromide ions leading to a higher intracellular concentration in these animals compared to their un-intoxicated counterparts who received a lucerne only diet.

5. Treatment with Potassium Bromide does not Alter Prevalence of Neurological Lesions Observed in Experimental Cases of Lolitrem B Intoxication Identification of early lesions associated with clinical presentation of experimental lolitrem B toxicity, and their correlation to lesions reported by us, and others, in naturally occurring field cases, was a key outcome of this study. The earliest lesions identified were restricted to the cerebellum and represent loss or dysfunction of neurons of the Purkinje layer and granule cell layer. The pyknotic nuclei observed in the granular layer of the cerebellum in this study likely represent evidence of granule neuron loss from this region, possibly via mechanisms of excitotoxic cell death, a finding that has not been reported previously (see FIG. 8). The relative prevalence was not found to be significantly altered in any bromide treatment group, despite some differences in prevalence between Groups 2 and 3 particularly. These data suggest that treatment with potassium bromide does not mitigate underlying neuropathological cell damage associated with lolitrem B toxicity despite alleviating some of the clinical signs of toxicosis. Thus, the mode of action of the KBr treatment is not yet known.

Mild changes were noted in animals from Group 5 (bromide prophylactic treatment only animals) where one animal showed signs of a fine tremor and 4 animals were observed to show mild alterations in stance such as abnormal foot placement at rest. Anxiolysis was also noted in 519 animals in this group such that they were more placid and easy to handle than their Group 1 counterparts and on occasion had to be encouraged to rise from rest in their pens.

No overt neurological signs were observed in any animal within the control group (Group 1). In those animals presenting with neurological signs associated with lolitrem B toxicosis, no significant difference was observed between timing of onset of clinical signs between groups 2 and 3. However a significant difference was observed between the onset of clinical signs between groups 3 and 4 (p=0.026) suggesting mild exacerbation of clinical presentation in these animals (see Table 4). Changes in body position (altered stance) was the major contributing factor to this result with altered stance being reported approximately two days earlier in this group than in their toxin-only counterparts (Groups 2 and 3, Table 3), A marginal increase was observed in the number of animals exhibiting truncal myoclonus compared to their toxin only counterparts, although this was not statistically significant. These data suggest that potassium bromide given at the prophylactic dose presented in this study is sufficient to induce mild mood changes in a significant proportion of animals although the penetration of this effect was variable and range of onset was wide (4-17 days; Table 3).

The findings in this study represent a significant breakthrough in available treatment options for the neurological deficits associated with perennial ryegrass toxicosis. The dramatic improvements in gait observed in this study and the ability to ablate tremor without sedation on delivery of an acute oral dose of potassium bromide are unique characteristics of this therapy. Its ease of administration and long half-life in the animal make it an ideal therapeutic intervention for this plant toxicity.

REFERENCES

Cheeks, P. R. (1995). Endogenous toxins amd mycotoxins in forage grasses and their effects on livestock. *Journal of Animal Science* 73(3): 909-918.

Combs, M., B. Rendell, K. Reed, W. Mace and J. Quinn (2014). Evidence of dehydration and electrolyte disturbances in cases of perennial ryegrass toxicosis in Australian sheep. *Australian Veterinary Journal* 92(4): 107-113.

Dixon, W. (1953). Processing data for outliers. *Biometrics:* 74-89.

Gibaldi, D. (1982). *Pharmacokinetics*. New York: Marcel Dekker Inc.

Mayhew, J. I. G. (2009). Large Animal Neurology. Oxford, United Kingdom, John Wiley and Sons Ltd.

Parton K, B. A Chambers J. P. (2006). Veterinary Clinical Toxicology, Massey University.

Podell, M. and Fenner, W. R. (1993). Bromide Therapy in Refractory Canine Idiopathic Epilepsy. *Journal of Veterinary Internal Medicine* 7(5): 318-327.

Reed, A. H., Henry, R. J., Mason, W. B. (1971). Influence of statistical method used on the resulting influence of normal range. *Clinical Chemistry* 17: 275-284.

Tietz N W. Analysis Of Drugs And Toxic Substances. In: Blanke R V, editor. *Fundamentals of clinical chemistry*. $2^{nd}$ edn. WB Saunders, Philadelphia, 1976: 1128-1129.

The invention claimed is:

1. A method of preparing an animal for grazing in a selected pasture to prevent symptoms of lolitrem B toxicity from developing in the animal during, or at completion of, grazing in the pasture, including administering a formulation including bromide to the animal selected for grazing in a selected pasture in an amount effective for preventing the animal from developing symptoms of lolitrem B toxicity before release of the animal to the pasture for grazing, wherein the formulation is administered to the animal orally, intravenously or intraperitoneally, and wherein the formulation includes bromide at a concentration of about 5 to about 70% w/w.

2. The method of claim 1, wherein the feed intake of the animal up to the time of administration of the formulation has been normal.

3. The method of claim 1, wherein the animal does not suffer grass toxicosis at the time of administration of the formulation.

4. The method of claim 1, wherein the animal does not have a movement disorder at the time of administration of the formulation.

5. The method of claim 1, wherein the animal is a ruminant.

6. The method of claim 5, wherein the ruminant is ovine or bovine.

7. The method of claim 1, wherein the formulation provides bromide in an amount of about 10 to about 750 mg/kg.

8. The method of claim 1, wherein the formulation is provided once daily for a period of one day to no more than about four weeks prior to releasing the animal to the selected pasture for grazing.

9. The method of claim 1 including the further step of administering a formulation including bromide to the animal after the animal has been released to the selected pasture for grazing.

10. The method of claim 9, wherein the formulation is administered for a period of one day to no more than two weeks from release of the animal to the selected pasture for grazing.

11. The method of claim 1, wherein the bromide is in the form of potassium bromide or magnesium bromide.

* * * * *